(12) United States Patent     (10) Patent No.: US 9,164,090 B2
Kim et al.     (45) Date of Patent: Oct. 20, 2015

(54) METHODS FOR DETECTING MOLECULAR INTERACTIONS

(75) Inventors: Tae Kook Kim, Daejeon (KR); Seung Goo Lee, Daejeon (KR); Sang Kyu Lee, Seoul (KR); Kyoung Hu Lee, Daejeon (KR); Jae-Seok Ha, Daejeon (KR)

(73) Assignees: Korea Advanced Institute of Science and Technology, Daejeon (KR); Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/671,881

(22) PCT Filed: Aug. 14, 2008

(86) PCT No.: PCT/KR2008/004761
§ 371 (c)(1),
(2), (4) Date: Jun. 15, 2010

(87) PCT Pub. No.: WO2009/025475
PCT Pub. Date: Feb. 26, 2009

(65) Prior Publication Data
US 2010/0273673 A1     Oct. 28, 2010

(30) Foreign Application Priority Data
Aug. 17, 2007 (KR) .......................... 10-2007-0082973

(51) Int. Cl.
*C12Q 1/68* (2006.01)
*A61K 38/00* (2006.01)
(Continued)

(52) U.S. Cl.
CPC ...... *G01N 33/54326* (2013.01); *G01N 33/5008* (2013.01); *G01N 33/536* (2013.01); *G01N 33/54346* (2013.01); *G01N 33/6845* (2013.01)

(58) Field of Classification Search
CPC ................... G01N 33/54326; G01N 33/5008; G01N 33/536; G01N 33/54346; G01N 33/6845
See application file for complete search history.

(56) References Cited

U.S. PATENT DOCUMENTS

| 4,200,690 A * | 4/1980 | Root et al. ................. 435/7.22 |
| 2003/0092029 A1 | 5/2003 | Josephson et al. |
| 2006/0148104 A1 | 7/2006 | Marini et al. |

FOREIGN PATENT DOCUMENTS

| WO | WO/2004/088313 | * 10/2004 |
| WO | 2006-009398 A1 | 1/2006 |

OTHER PUBLICATIONS

Won et al., A Magnetic Nanoprobe Technology for Detecting Molecular Interactions in Live Cells, Science vol. 309 Jul. 1, 2005.*

(Continued)

*Primary Examiner* — Reza Ghafoorian
(74) *Attorney, Agent, or Firm* — Rabin & Berdo P.C.

(57) ABSTRACT

The present invention relates to methods for dynamically detecting the interactions between various materials including bioactive molecules and for detecting target molecules. More specifically, the present invention relates to a method for dynamically detecting bait-prey interactions and a method for easily detecting target molecules which blocks or activates the interactions, the method comprising: allowing a material capable of forming a nano-assembly matrix, a bait and a prey to interact with each other, and analyzing whether a nano-assembly matrix is formed by the interaction between the bait and the prey in vitro or in vivo; or allowing a material capable of forming a nano-assembly matrix, a bait and a prey to interact with each other, inducing the formation of a nano-assembly matrix by a mediator (regulator) material in vitro or in vivo, and then analyzing whether the prey and the bait co-localizes on the nano-assembly matrix.

36 Claims, 19 Drawing Sheets
(19 of 19 Drawing Sheet(s) Filed in Color)

(51) Int. Cl.
G01N 33/543 (2006.01)
G01N 33/50 (2006.01)
G01N 33/536 (2006.01)
G01N 33/68 (2006.01)

(56) References Cited

OTHER PUBLICATIONS

Chakrabarti et al.,Transfer of monoclonal antibodies into mammalian cells by electroporation, The Journal of Biological Chemistry, vol. 264, No. 26, Issue of Sep. 15, pp. 15494-15500, 1989.*
Lewin et al., Tat peptide-derivatized magnetic nanoparticles allow in vivo tracking and recovery of progenitor cells, Nature Biotechnology vol. 18 Apr. 2000.*
Lee et al., A novel approach to ultrasensitive diagnosis using supramolecular protein nanoparticles, FASEB J. 21, 1324-1334 (2007).*
Berg, Modulation of Protein-Protein Interactions with Small Organic Molecules, Angew. Chem. Int. Ed. 2003, 42, 2462-2481.*
Joseph Schlessinger, Ligand-Induced, Receptor-Mediated Dimerization and Activation of EGF Receptor, Cell, vol. 110, 669-672, Sep. 20, 2002.*
Chen et al., Site specific labeling of cell surface proteins with biophysical probes using biotin ligase, Nature Methods, vol. 2, No. 2, Feb. 2005.*
Wouters, Fluorescence lifetime imaging of receptor tyrosine kinase activity in cells, Current Biology vol. 9 No. 19, Jul. 1999.*
Scheffel et al., An acidic protein aligns magnetosomes along a filamentous structure in magnetotactic bacteria, Nature, vol. 440:Mar. 2, 2006.*
Ashburn, T. et al., "Drug Repositioning: Identifying and Developing New Uses for Existing Drugs," Nature Reviews, vol. 3, pp. 673-683 (Aug. 2004).
Asian, K. et al., "Microwave-Accelerated Ultrafast Nanoparticle Aggregation Assays Using Gold Colloids," Anal. Chem., 79, pp. 2131-2136 (2007).
Burdine, L. et al., "Target Identification in Chemical Genetics: The (Often) Missing Link," Chemistry & Biology, vol. 11, pp. 593-597 (May 2004).
Chasteen, N. D., et al., "Mineralization in Ferritin: An Efficient Means of Iron Storage," Jrl. of Structural Biology, vol. 126, pp. 182-194 (1999).
Clardy, J. et al., "Lessons from natural molecules," Nature, vol. 432, pp. 829-837 (Dec. 16, 2004).
Elghanian, R. et al., "Selective Colorimetric Detection of Polynucleotides Based on the Distance-Dependent Optical Properties of Gold Nanoparticles," Science, vol. 277, pp. 1078-1080 (Aug. 22, 1997).

Hirsch, L.R. et al., "A Whole Blood Immunoassay Using Gold Nanoshells," Anal. Chem., 75, pp. 2377-2381 (2003).
Licitra, E. J. et al., "A three-hybrid system for detecting small ligand-protein receptor interactions," Proc. Natl. Acad. Sci. USA, vol. 93, pp. 12817-12821 (Nov. 1996).
Mendelsohn, A. et al., "Protein Interaction Methods—Toward an Endgame," Science, vol. 284, No. 5422, pp. 1948-1950 (Jun. 18, 1999).
Moshinsky, D. et al., "A Widely Applicable, High-Throughput TR-FRET Assay for the Measurement of Kinase Autophosphorylation: VEGFR-2 as a Prototype," Jrl. of Biomolecular Screening, 8(4), pp. 447-452 (2003).
Perez, J. M. et al., "Magnetic relaxation switches capable of sensing molecular interactions," Nature Biotechnology, vol. 20, pp. 816-820 (Aug. 2002).
Phizicky, E.M. et al., "Protein-Protein Interactions: Methods for Detection and Analysis," Microbiological Reviews, vol. 59, No. 1, pp. 94-123 (Mar. 1995).
Sche, P. et al., "Display cloning: functional identification of natural product receptors using cDNA-phage display," Chem. Biol., 6:707 (1999).
Stockwell, B.. "Exploring biology with small organic molecules," Nature, vol. 432, pp. 846-854 (Dec. 16, 2004).
Strausberg, R. et al., "From Knowing to Controllling: A Path from Genomics to Drugs Using Small Molecule Probes," Science, vol. 300, pp. 294-295 (Apr. 11, 2003).
Won, J. et al., "A Magnetic Nanoprobe Technology for Detecting Molecular Interactions in Live Cells," Science, vol. 309, pp. 121-123 (Jul. 1, 2005).
Zheng, X. S. et al., "Genetic and Genomic Approaches to Identify and Study the Targets of Bioactive Small Molecules," Chemistry & Biology, vol. 11, pp. 609-618 (May 2004).
Supplementary European Search Report for European Application No. EP 08793275, dated Jan. 28, 2011.
Sangkyu Lee et al., "Inducible Biosynthetic Nanoscaffolds as Recruitment Platforms for Detecting Molecular Target Interactions inside Living Cells", Journal of the American Chemical Society, Jun. 26, 2012, pp. 11346-11349, vol. 134.
Hee Won Yang et al., "Cooperative Activation of PI3K by Ras and Rho Family Small GTPases", Molecular Cell, Jul. 27, 2012, pp. 1-10, vol. 47.
James B. Delehanty et al., "Elaborate Nanoparticle-Based Traps for Catching Cytosolic Players in the Act", ChemBioChem, 2012, pp. 30-33, vol. 13.
Sangkyu Lee et al., "Small-Molecule-Based Nanoassemblies as Inducible Nanoprobes for Monitoring Dynamic Molecular Interactions Inside Live Cells", Angew. Chem. Int. Ed. 2011, pp. 8709-8713, vol. 50.

\* cited by examiner

FIG. 2
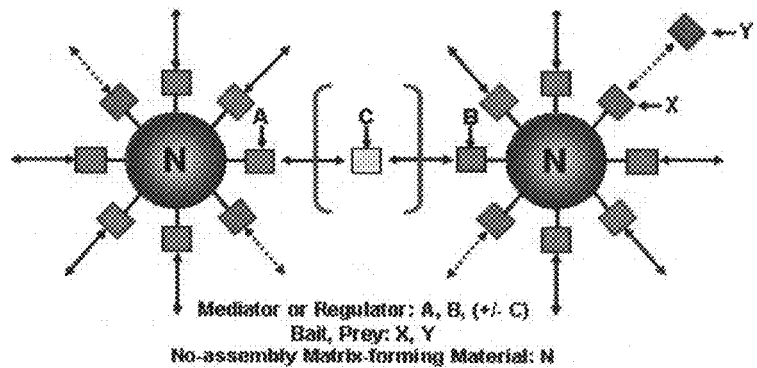
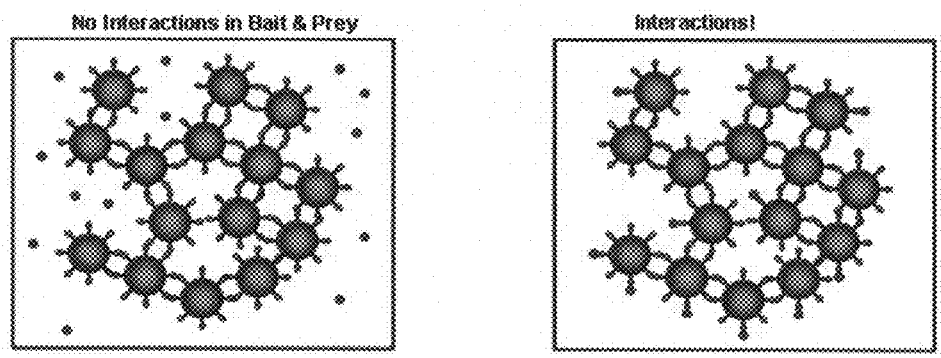
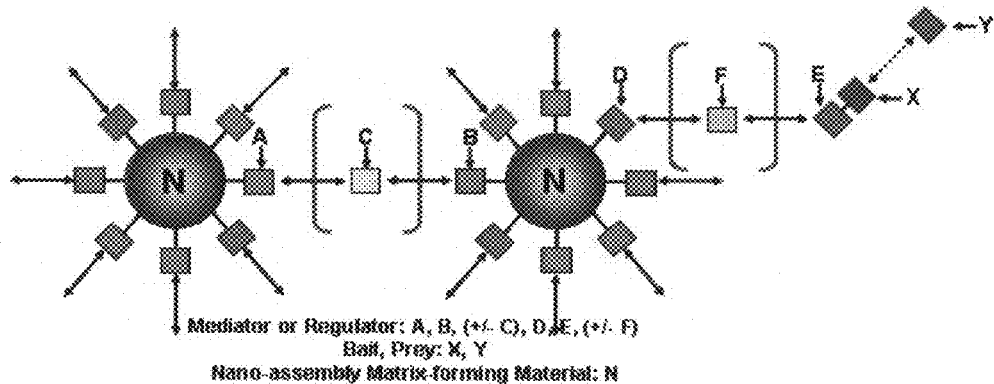
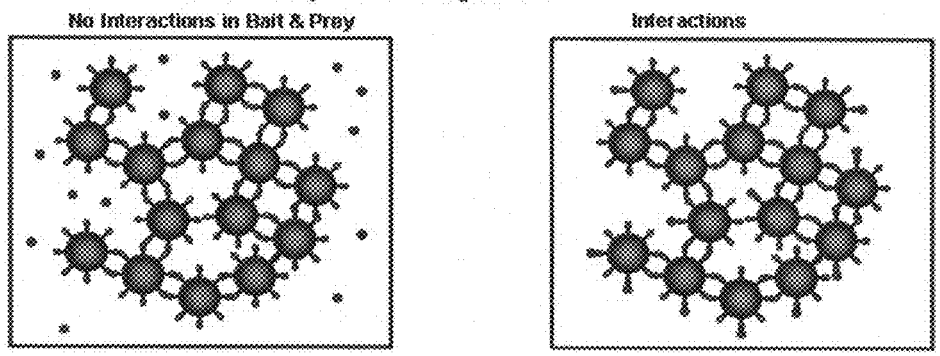

FIG. 26
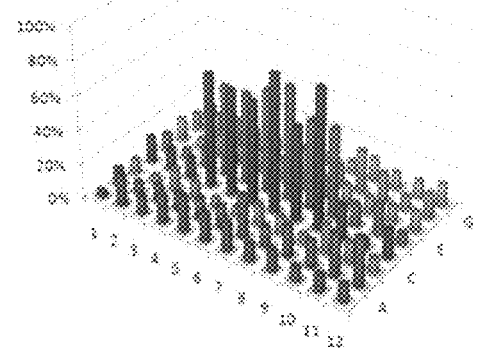
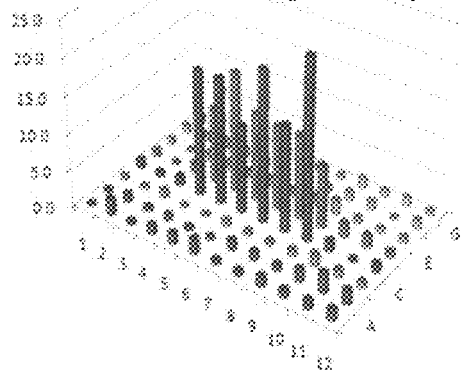
FIG. 27
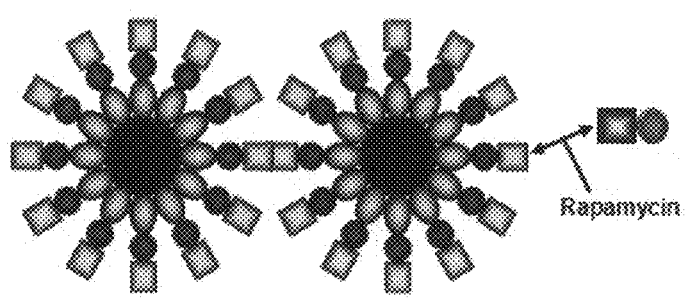

METHODS FOR DETECTING MOLECULAR INTERACTIONS

CROSS-REFERENCES TO RELATED APPLICATIONS

This application is a U.S. national phase application, pursuant to 35 U.S.C. §371 of PCT/KR2008/004761, filed Aug. 14, 2008, designating the United States, which claims priority to Korean Application No. 10-2007-0082973, filed Aug. 17, 2007. The entire contents of the aforementioned patent applications are incorporated herein by this reference.

TECHNICAL FIELD

The present invention relates to a method for detecting the dynamic interactions between various bioactive molecules in cells and to a method for detecting molecules which regulate the interactions and functions of the bioactive molecules.

BACKGROUND ART

In general, various physiological functions are regulated by the dynamic interactions between various bioactive molecules. If such interactions do not occur properly, problems arise to cause diseases. For example, proteins in vivo perform their functions by interaction with other proteins. Generally, two proteins having complementary structures interact with each other, and a bioactive compound interacts specifically with the specific portion of the three-dimensional protein structure. Generally, the interaction between two proteins strongly implies that they are functionally related. Furthermore, a bioactive compound interacting specifically with the specific portion of a disease-associated protein has potential as a therapeutic agent which can diagnose, prevent, treat or alleviate the disease by controlling the activity of the protein.

Accordingly, in the field of new drug development, various methods for detecting novel target proteins or screening bioactive molecules as drug candidates by detecting the interaction between a "bait" whose function and feature are known and a "prey" which is an interaction partner to be analyzed and detected have been studied. Thus, the identification and isolation of a novel target protein through the analysis of the interaction between bioactive molecules are considered as very important research projects for obtaining useful information about the activity, effectiveness and adverse effects of bioactive compounds. Additionally, target proteins promote the understanding of biological pathways and signal transduction systems and provide information on fundamental cellular regulation and disease mechanisms. Such information is a very powerful tool for developing new drugs, improving existing drugs and discovering the novel pharmaceutical use of existing drugs by analyzing and detecting bioactive compounds which interact with the target proteins.

Modern medicine faces the challenge of developing safer and more effective therapies. However, many drugs currently in use are prescribed by the biological effects in disease models without their target proteins and molecular targets (L. Burdine et al., Chem. Biol. 11:593, 2004; J. Clardy et al., Nature 432:829, 2004). Bioactive natural products are an important source for drug development, but their mode of action are usually unknown (J. Clardy et al., Nature 432:829, 2004). Elucidation of their physiological targets and molecular targets is essential for understanding their therapeutic and adverse effects, thereby enabling the development of improved second-generation therapeutics. Moreover, the discovery of novel targets of clinically proven compounds may suggest new therapeutic applications (T. T. Ashburn et al., Drug Discov. 3:673, 2004).

In chemical-biological field employing high-throughput cell-based screening, "target screening" is used to identify small molecules with a desired phenotype from large compound libraries (R. L. Strausberg et al., Science 300:294, 2003; B. R. Stockwell, Nature 432:846, 2004). Despite the great benefits of such screening, this approach has been hampered by the daunting task of target identification. However, the development of such identification technology is very important in various bioscience fields, including genomics, proteomics and system biology, because effective detection of diverse intracellular molecular interactions, including protein (or small molecule)-protein, is essential for understanding dynamic biological processes and regulatory networks.

In the field of target screening, several technologies, including affinity chromatography (Phizicky, E. M. et al., Microbiol. Rev., 59:94, 1995; Mendelsohn A. R. et al., Science, 284:1948, 1999), protein-small molecule microarray, phage display (Sche, P. P. et al., Chem. Biol., 6:707, 1999), yeast two-/three-hybrid assay (Licitra, E. J. et al., Proc. Natl. Acad. Sci. USA, 93:12817, 1996), expression profiling, and parallel analysis of yeast strains with heterologous deletions (Zheng et al., Chem. Biol., 11: 609, 2004), have been used to analyze interactions between bioactive molecules. However, such technologies all suffer from diverse problems, including high background, false positives, low sensitivity, inappropriate folding after protein expression, indirectness, lack of modification after protein expression, or limited target accessibility including cellular compatibility. In addition, the use of artificial experimental milieu, such as in vitro binding conditions or non-mammalian cells, sometimes causes errors in experimental results.

Accordingly, it is most preferable to directly examine the interaction between bioactive molecules in a state in which high sensitivity and selectivity were considered in physiological or pharmaceutical terms. Technologies for probing molecular interactions within living mammalian cells such as fluorescence resonance energy transfer (FRET) (Moshinsky, D. J. et al., Screen., 8(4): 447, 2003) or protein-fragment complementation assay (PCA) are available, but they are limited by the requirements for specific spatial orientation or distance between the interaction partners.

Thus, it is considered that it is very important to develop the above-described base technology in order to offer various advantages over the prior art.

First, by probing the interactions between physiologically or pharmaceutically relevant bioactive substances or molecules, misleading outcomes produced by an artificial experimental setting can be greatly diminished. Second, it is possible to directly translate the interaction between bioactive molecules into a clear readout signal, unlike indirect readout methods that are dependent on overall expression profiles or complex biological phenotypes. Thus, intrinsic false positives/negatives or error-prone deductions about bioactive molecules and molecular targets can be obviated. Third, it is possible to perform dynamic, single-cell analysis for the interactions between bioactive molecules. Dynamic analysis of individual living cells provides an effective method which can analyze intracellular processes occurring non-simultaneously among heterogeneous cells, over a broad range in physiological and pharmaceutical terms.

Therefore, the above-described base technology can be used to detect a variety of biological interactions (e.g., interaction between a bioactive small molecule and a protein) and protein modifications (e.g., phosphorylation) within living cells in a broad range of tissues and disease states.

In order to satisfy the requirements of the above-described base technology and solve the problems occurring in the prior art, the present inventors have studied a method for dynamically analyzing the interactions between bioactive molecules not only in vitro, but also in vivo. As a result, the present inventors have found that the interactions between bioactive molecules can be analyzed and detected by analyzing whether the interactions between various bioactive molecules result in the formation of a nano-assembly matrix or the bioactive molecules co-locate on the nano-assembly matrix, thereby completing the present invention.

SUMMARY OF INVENTION

It is an object of the present invention to provide a method for directly detecting the interaction between a bait, which is a specific bioactive molecule, and a prey, which is a bioactive molecule to be detected, and a method for detecting the prey which interacts with the bait.

Another object of the present invention is to provide a method for analyzing and detecting a target molecule which blocks, inhibits, activates or induces the interaction between the bait and the prey.

To achieve the above objects, in a first embodiment, the present invention provides a method for detecting molecular interactions, the method comprising the steps of: (i) providing a nano-assembly matrix-forming material, a bait and a prey to the same field or system; (ii) forming a nano-assembly matrix by the interaction between the bait and the prey; and (iii) examining whether the nano-assembly matrix was formed, thus detecting the bait-prey interaction. Herein, the bait-prey interaction is detected by analyzing whether the prey interacts with the bait to form the nano-assembly matrix.

In a second embodiment, the present invention provides a method for detecting molecular interactions, the method comprising the steps of: (i) providing mediator (regulator) materials and a nano-assembly matrix-forming material having a bait bound thereto, to the same field or system; (ii) forming a nano-assembly matrix by the interaction between the mediator materials; (iii) providing a prey to the formed nano-assembly matrix; and (iv) measuring the binding location of the prey by interaction with the bait present on the formed nano-assembly matrix so as to determine whether the prey co-localizes with the bait, thus detecting the bait-prey interaction. Herein, the molecular interaction is detected by analyzing whether the prey co-localizes with the bait on the nano-assembly matrix.

In a third embodiment, the present invention provides a method for detecting molecular interactions, comprising the steps of: (i) providing a nano-assembly matrix-forming material having first mediator (regulator) materials bound thereto, and a bait having second (regulator) materials bound thereto, to the same field or system; (ii) forming nano-assembly matrix by the interaction between the first mediator (regulator) materials and binding the bait to the formed nano-assembly matrix by the interaction between the second mediator materials; (iii) providing a prey to the formed nano-assembly matrix; and (iv) measuring the binding location of the prey by interaction with the bait bound to the formed nano-assembly so as to determine whether the prey co-localizes with the bait, thus detecting the bait-prey interaction. Herein, the bait-prey interaction is by analyzing whether the prey co-localizes with the bait on the nano-assembly matrix.

Furthermore, the present invention provides a method for detecting a target molecule which blocks (inhibits) or activates (induces) the interaction between the bait and the prey.

Other features and embodiments of the present invention will become more apparent from the following detailed description and the appended claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

In FIG. 1, X, Y and A are the same or different materials, and N is a nano-assembly matrix-forming material.

The upper figure of FIG. 2 is a schematic diagram showing a construct according to a second method of the present invention for detecting the interaction between probes X and Y when the formation of a nano-assembly matrix is induced by the direct interaction between A and B or the indirect interaction between A and B through C. In FIG. 2, A, B and C are the same or different materials, X and Y are the same or different materials, and N is a nano-assembly matrix-forming material.

The lower figure of FIG. 2 is a schematic diagram showing a construct according to a third method of the present invention for detecting the interaction between X and Y when the formation of a nano-assembly matrix is induced by the interactions between first mediator (regulator) materials A, B, C and D while a detection material X binds to the formed nano-assembly matrix by the interaction between second mediator (regulator) materials E and F. Herein, A B, C and D are the same or different materials, E and F are the same or different materials, X and Y are the same or different materials, and N is a nano-assembly matrix-forming material.

Figure 3:
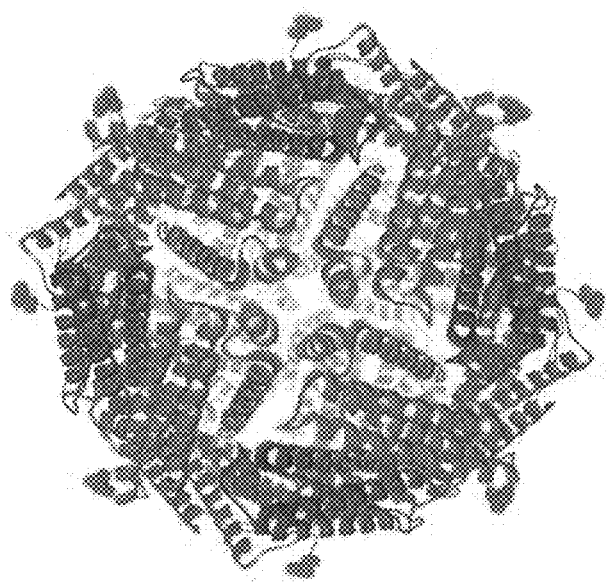

FIG. 3 shows the structure of a nano-sized unit matrix formed by the self-assembly of ferritin protein.

Figure 4:
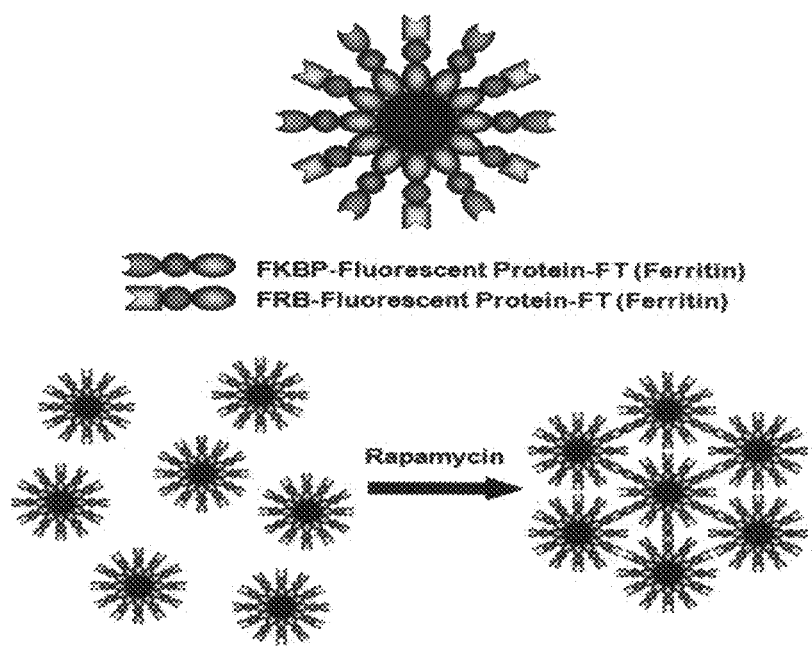

FIG. 4 is a schematic diagram showing that detection materials FKBP and FRB interact with each other by a mediator Rapamycin to form a nano-assembly matrix.

Figure 5:
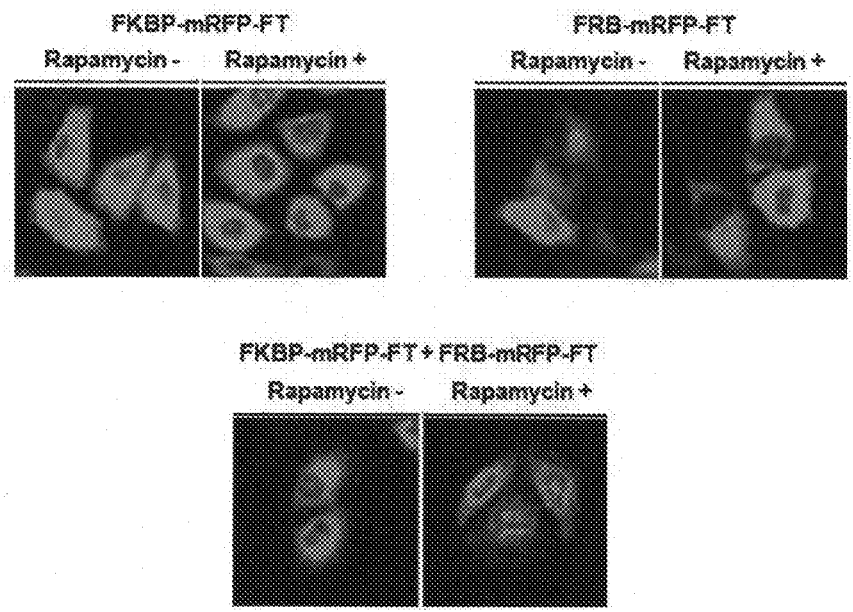

FIG. 5 is a fluorescence micrograph showing the formation of a nano-assembly matrix by an FKBP-FRB interaction in cells.

Figure 6:
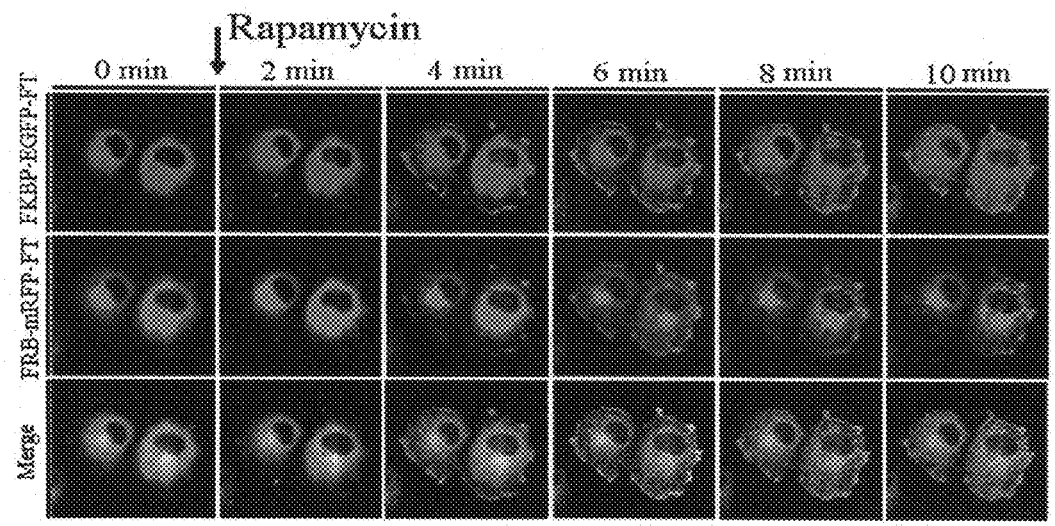

FIG. 6 is a confocal micrograph showing the formation of a nano-assembly matrix by an FKBP-FRB interaction at various points of time.

Figure 7:
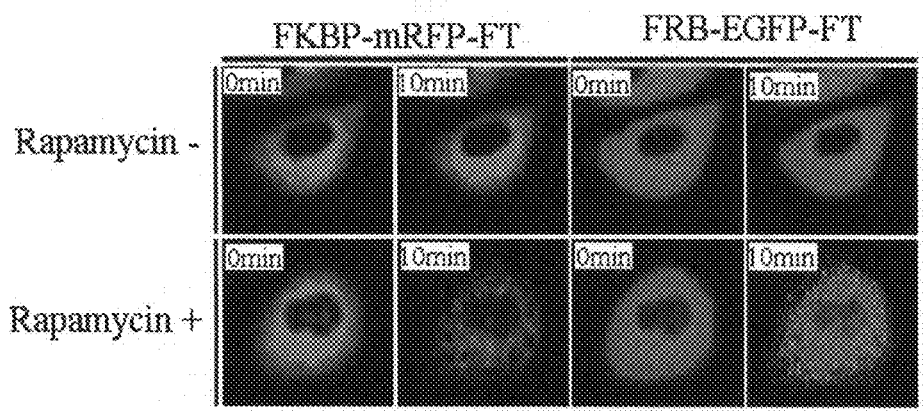

FIG. 7 is a fluorescence micrograph showing a case in which fluorescent proteins bound to FKBP and FRB were exchanged with each other.

Figure 8:
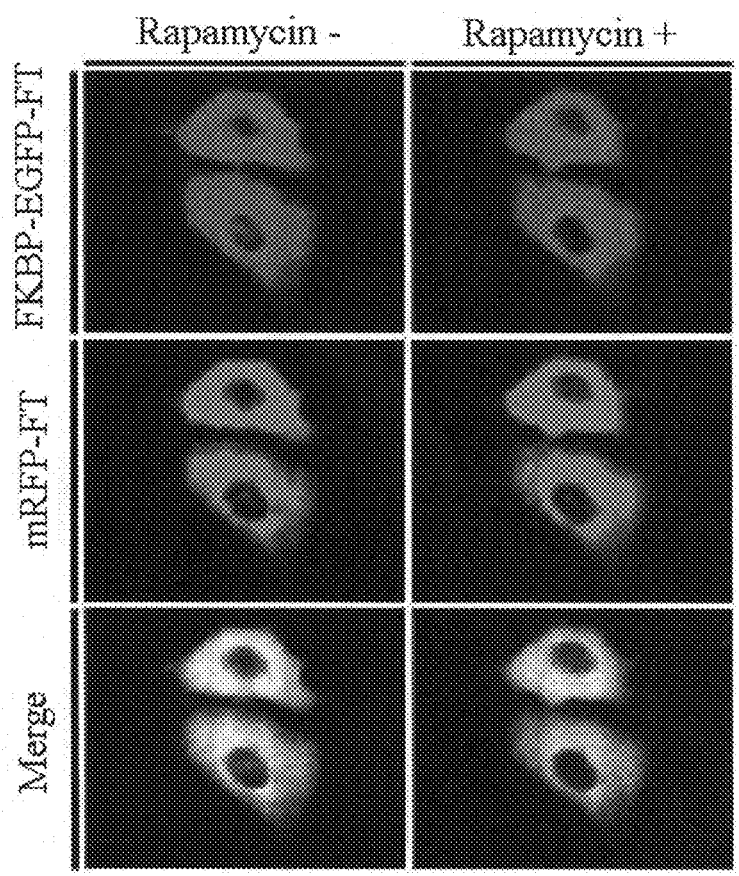
Figure 9:
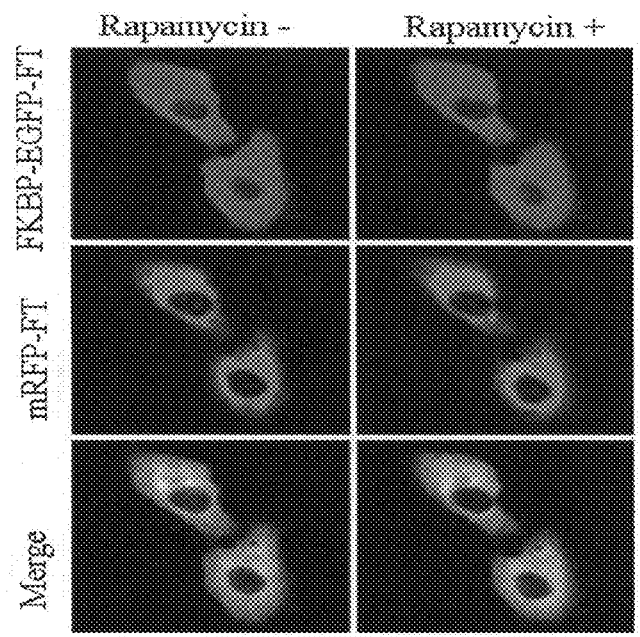

FIG. 8 and FIG. 9 are fluorescence micrographs showing a specific interaction between two proteins FKBP and FRB.

Figure 10:
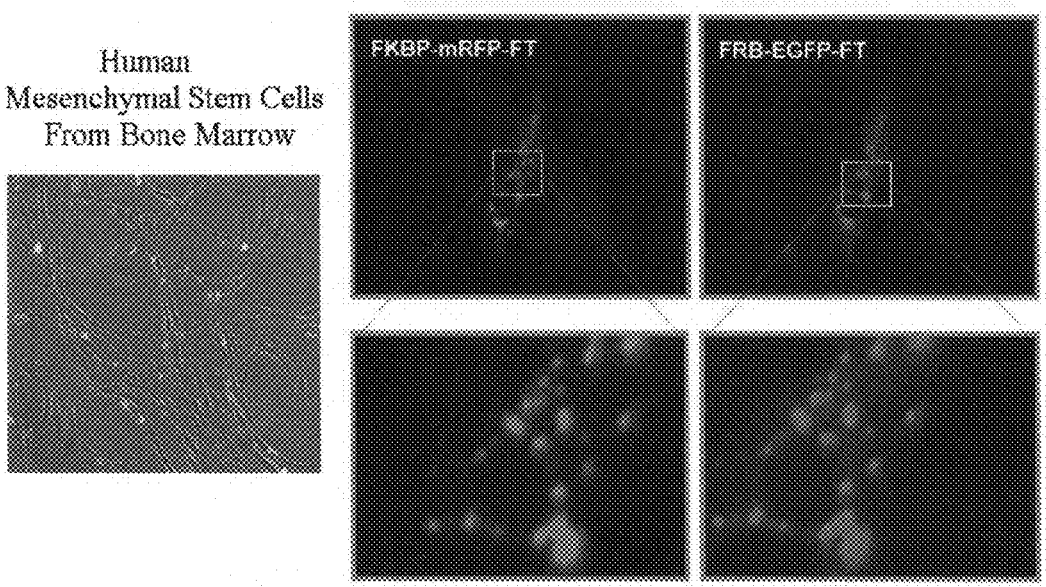

FIG. 10 is a fluorescence micrograph showing the formation of a nano-assembly matrix by an FKBP-FRB interaction in human stem cells.

Figure 11:
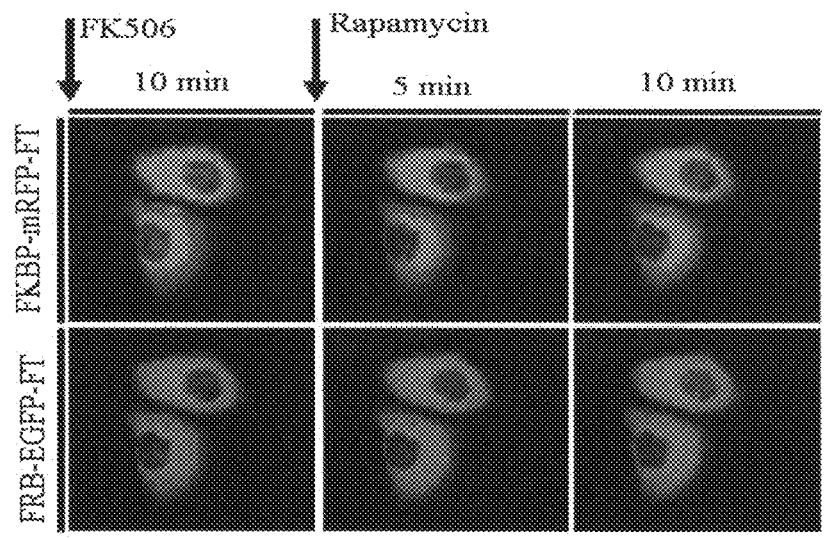

FIG. 11 is a fluorescence micrograph showing a case in which FK506 was treated with a competitive compound for Rapamycin.

Figure 12:
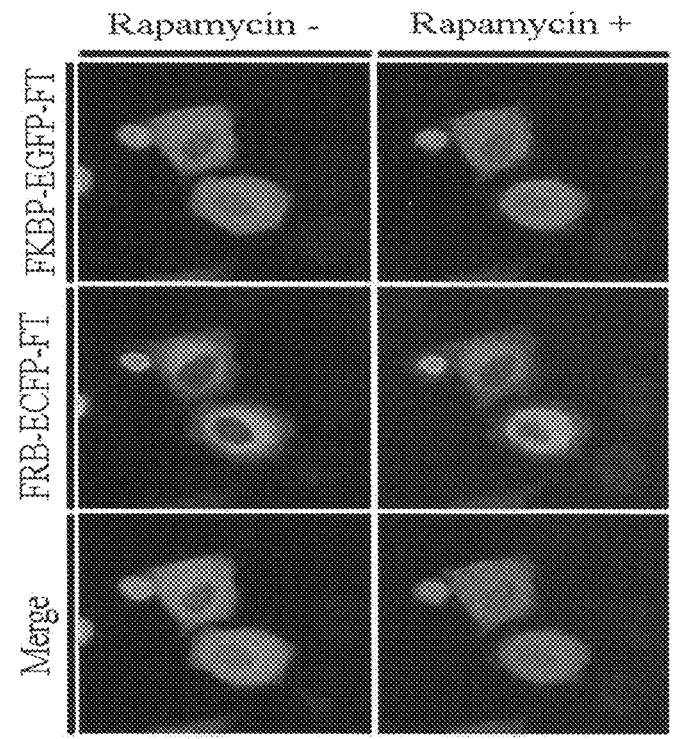
Figure 13:
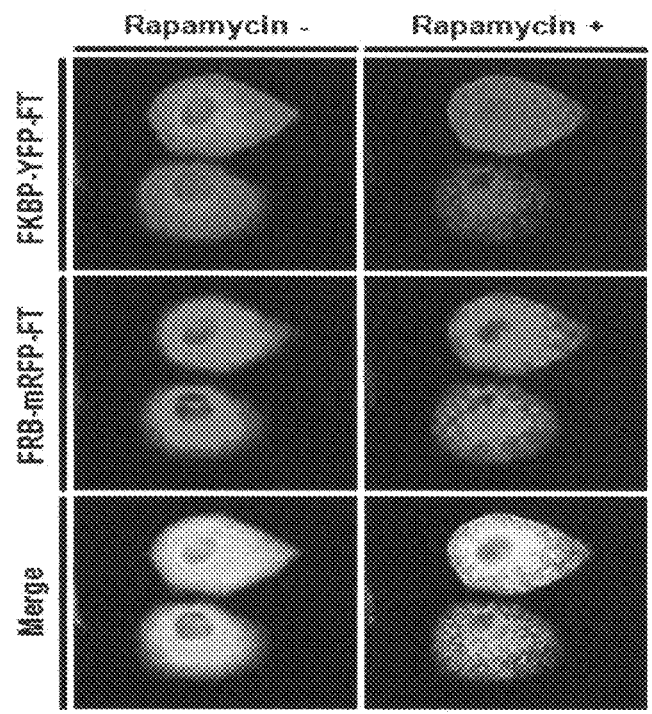

FIG. 12 and FIG. 13 are fluorescence micrographs showing observation results for the influence of adhesion of various fluorescent proteins.

Figure 14:
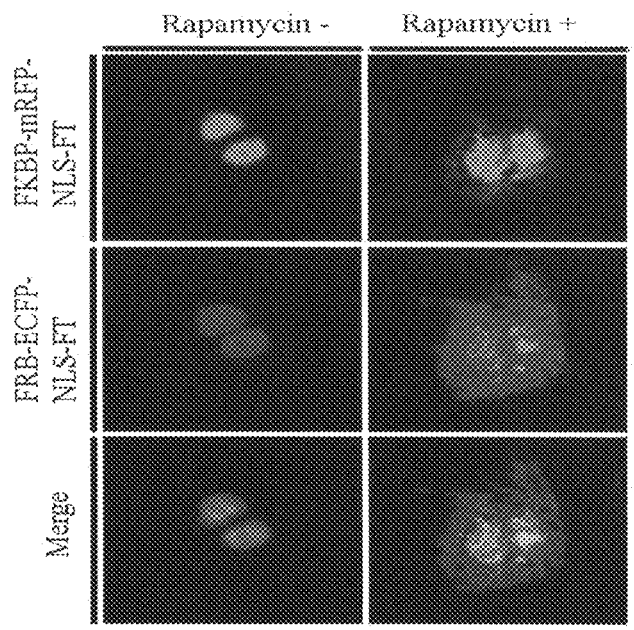

FIG. 14 is a fluorescence micrograph showing the formation of a nano-assembly matrix by an FKBP-FRB interaction in nuclei using a ferritin protein having NLS (nuclear localization signal) attached thereto.

Figure 15:
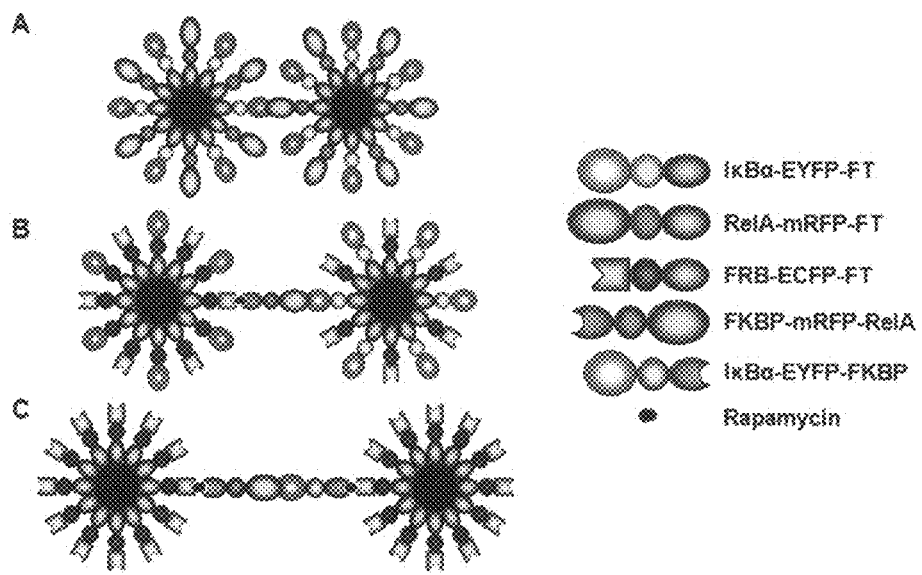

FIG. 15 is a schematic diagram showing that detection materials of IkBα and RelA interact with each other in various ways (A, B and C) to form nano-assembly matrices.

Figure 16:
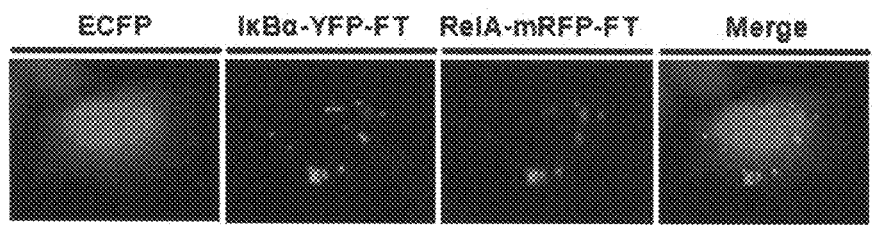

FIG. 16 is a fluorescence micrograph showing the formation of a nano-assembly matrix by the interaction between IkBα and RelA proteins as in the case of FIG. 15A.

Figure 17:
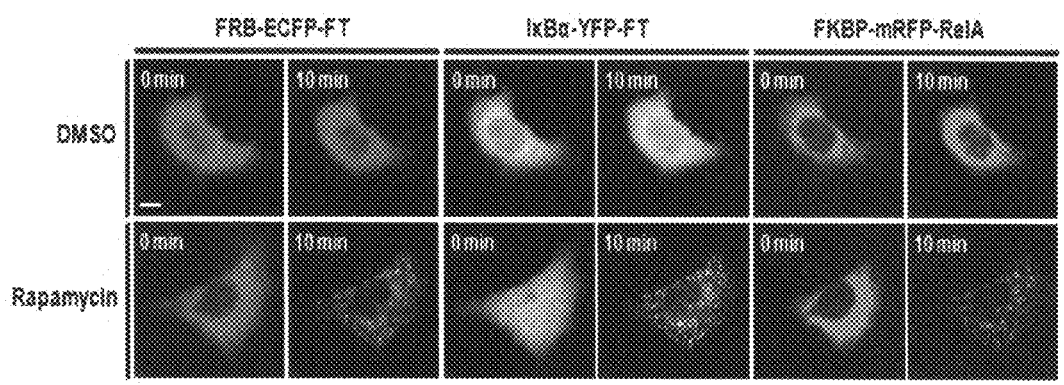

FIG. 17 is a fluorescence micrograph showing the formation of a nano-assembly matrices by the interaction between FRB and FKBP and the interaction between IkBα and RelA, treated with Rapamycin as in the case of FIG. 15B.

Figure 18:
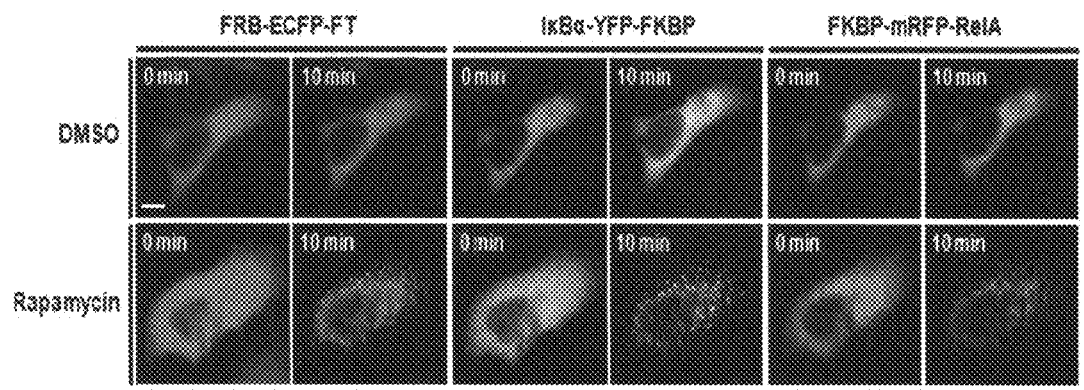

FIG. 18 is a fluorescence microscope showing the formation of onather large nano-assembly matrices by the interaction between FRB and FKBP and the interaction between IkBα and RelA, treated with Rapamycin as in the case of FIG. 15B.

Figure 19:
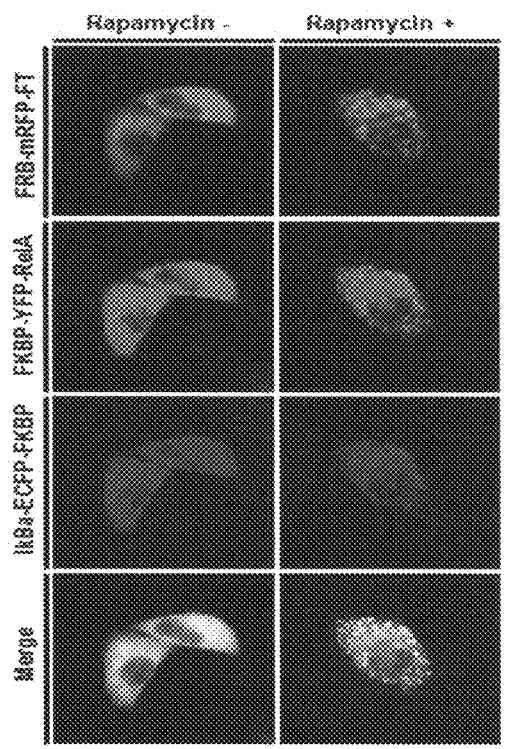

FIG. 19 is a fluorescence micrograph showing the influence of various fluorescent proteins.

Figure 20:
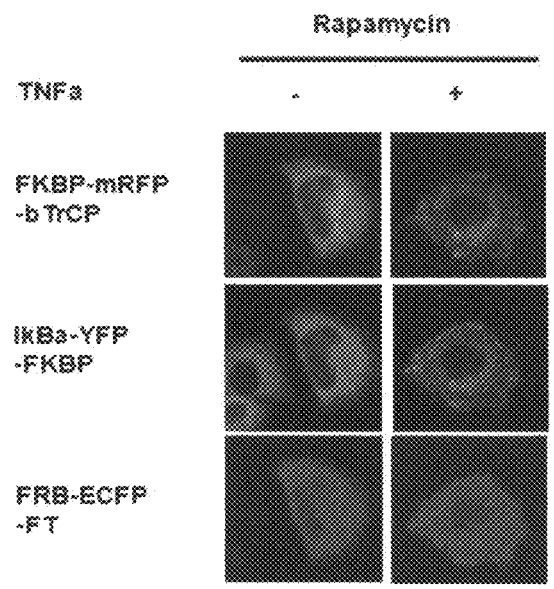

FIG. 20 is a fluorescence micrograph showing the formation of large nano-assembly matrices by the interaction between FRB and FKBP, treated with Rapamycin, and the interaction between IkBα and bTrCP, treated with physiological signal TNFa.

Figure 21:
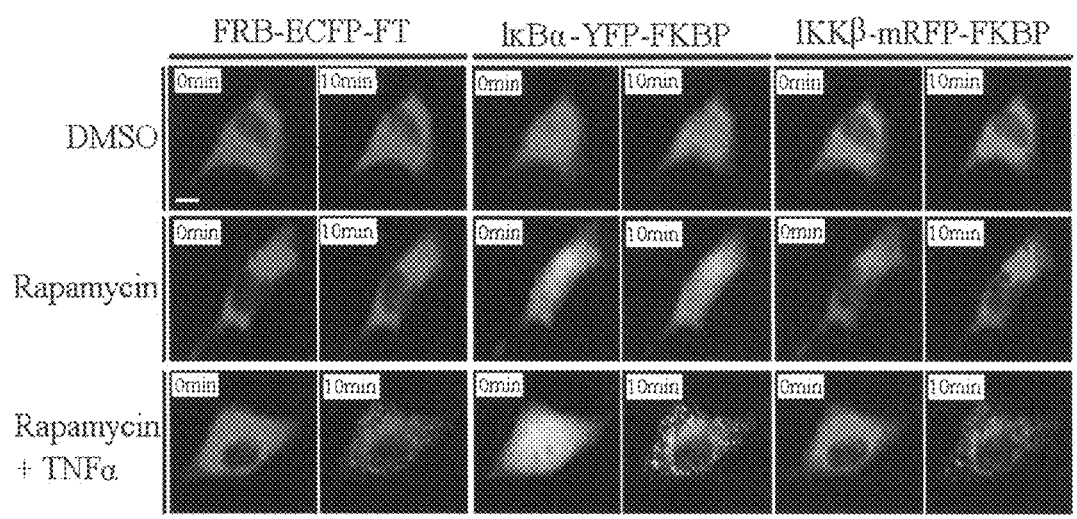

FIG. 21 is a fluorescence micrograph showing the formation of a large nano-assembly matrix according to an IKKb-IkBα interaction by TNFa.

Figure 22:
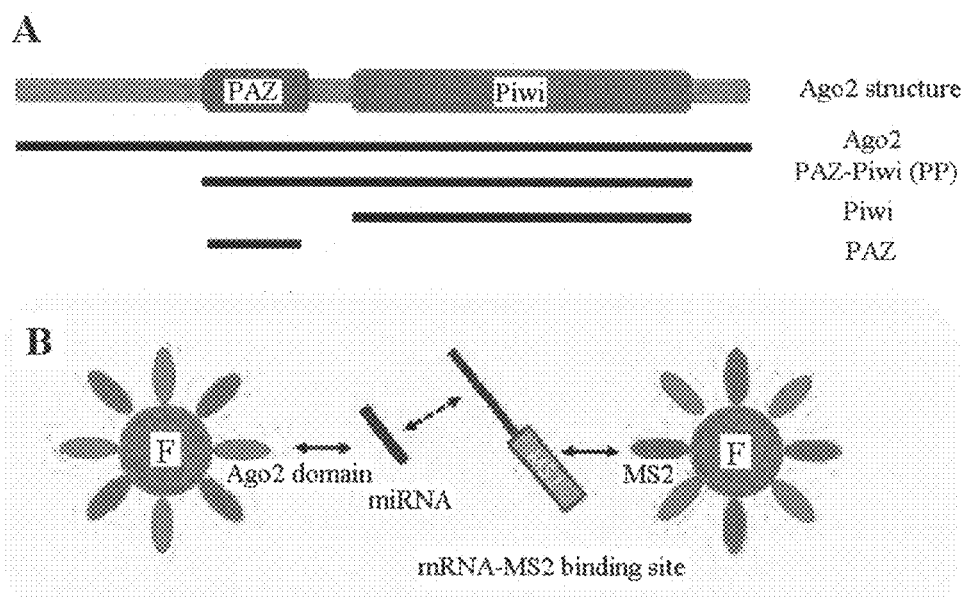

FIG. 22 is a schematic diagram showing the formation of a large nano-assembly matrix through multiple interactions between RNA and a regulator protein by a ferritin fusion protein.

Figure 23:
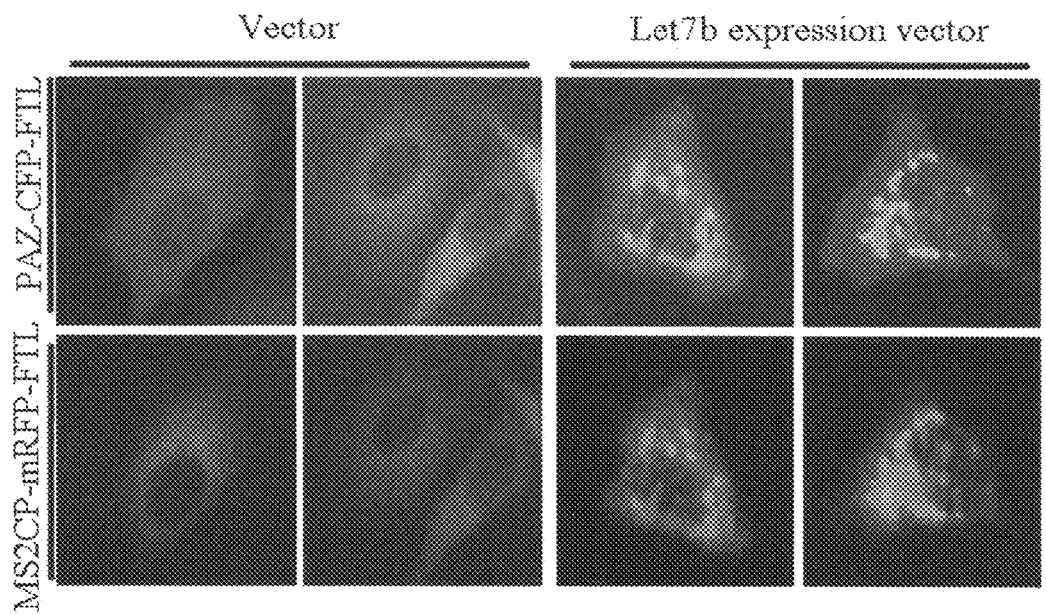

FIG. 23 is a fluorescence micrograph showing the formation of large nano-assembly matrices by the binding of PAZ with miRNA, the binding of let-7b (miRNA) with lin28-MS2bs (mRNA) and the binding of lin28-MS2bs(mRNA) with MS2CP.

Figure 24:
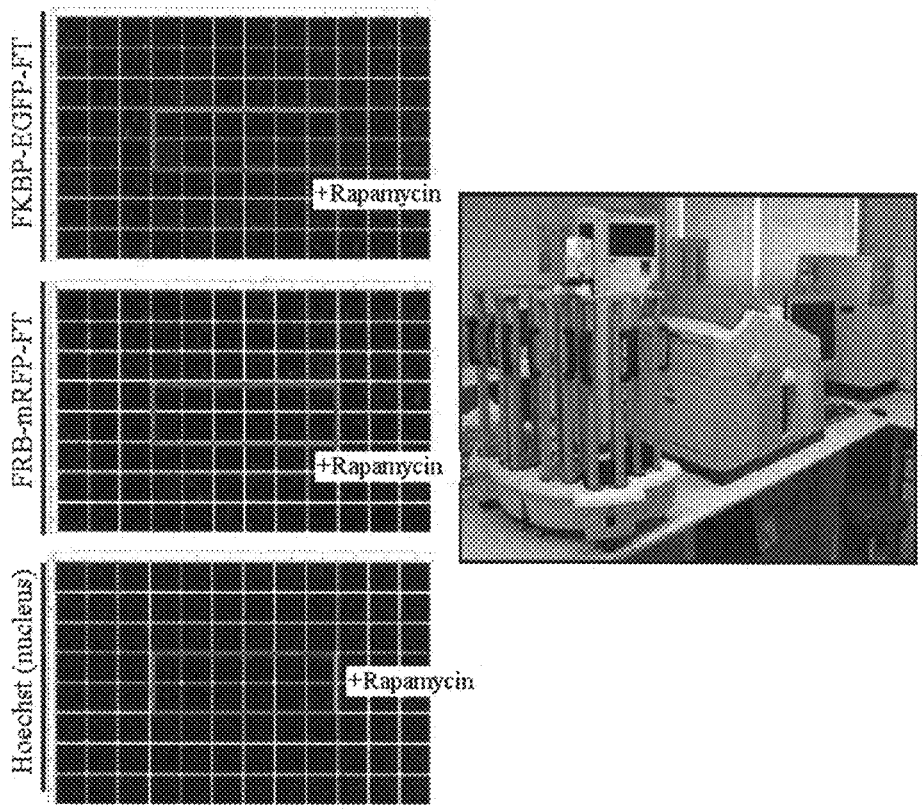
Figure 25:
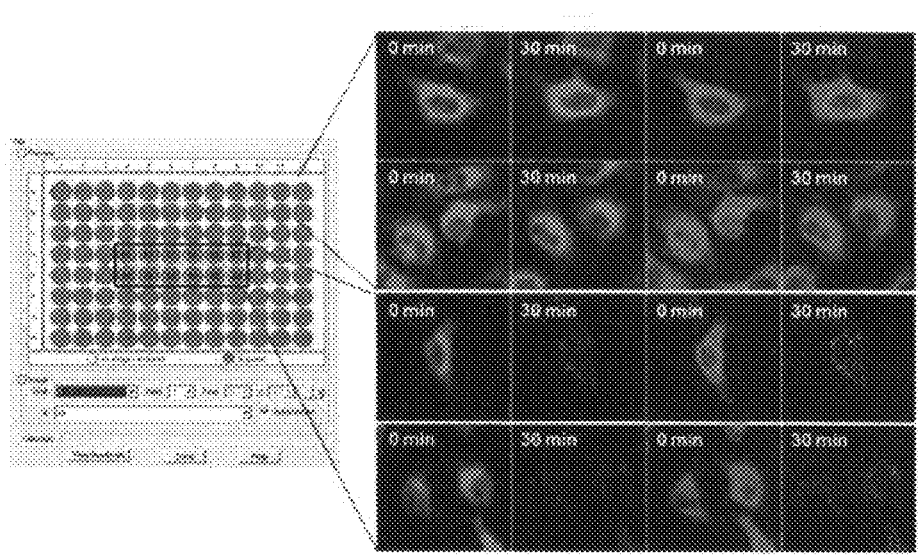

FIG. 24 and FIG. 25 are fluorescence micrographs showing that the formation of a nano-assembly matrix according to an FRB-FKBP interaction by Rapamycin in a 96-well plate was imaged at high speed using In-Cell Analyzer 1000(GE).

FIG. 26 is a graphic diagram showing results obtained by quantitatively analyzing the imaging results using an algorithm of In-Cell Developer (GE).

FIG. 27 is a schematic diagram showing the formation and docking of a nano-assembly matrix by a specific mutation (mt) of FKBP protein and an FRB-FKBP interaction.

Figure 28:
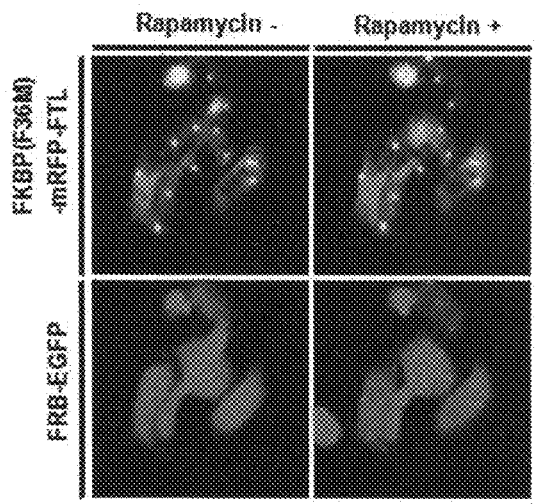

FIG. 28 is a fluorescence micrograph showing the formation and docking of a nano-assembly matrix by a specific mutation (mt) of FKBP protein and an FRB-FKBP interaction.

Figure 29:
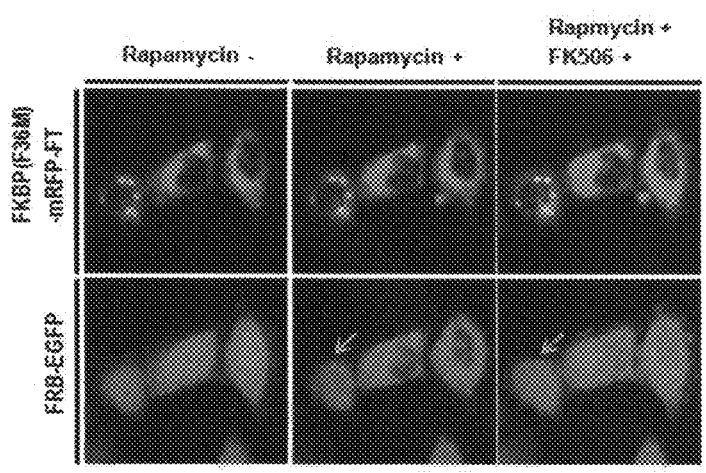

FIG. 29 is a fluorescence micrograph showing the inhibitory effect of a competitive compound FK506 on docking to the surface of the nano-assembly matrix of FIG. 28.

Figure 30:
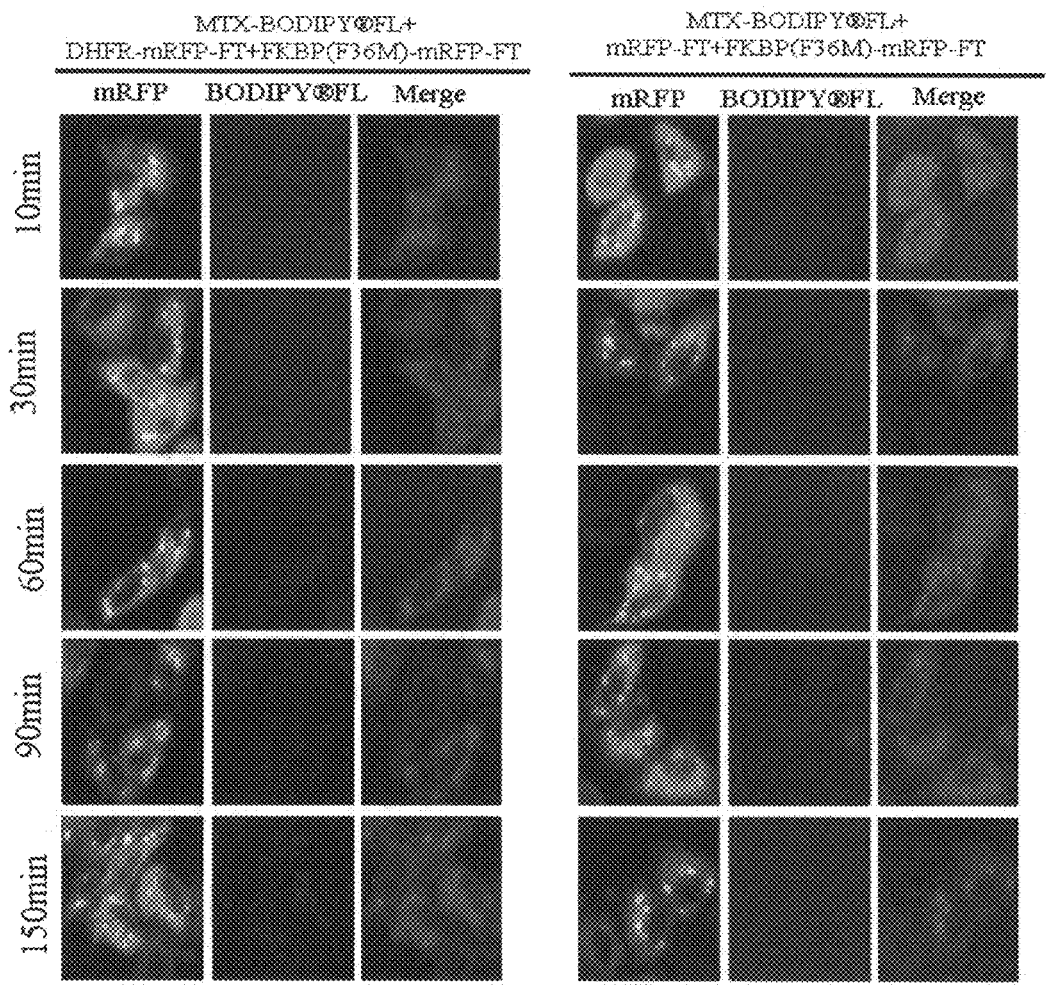
Figure 31:
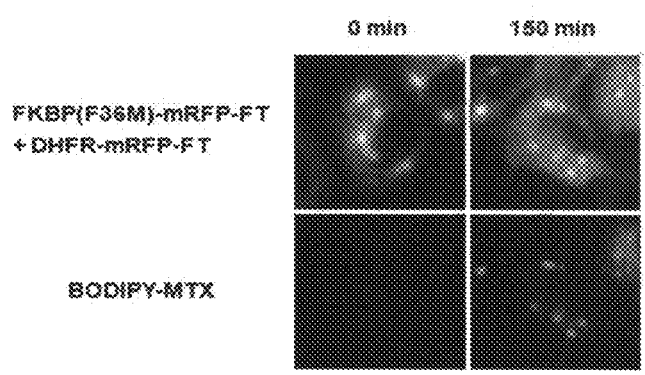

FIG. 30 and FIG. 31 are fluorescence micrographs showing the formation and docking of a nano-assembly matrix by an FKBP(F36M) mutation and a DHFR protein-MTX compound interaction.

Figure 32:
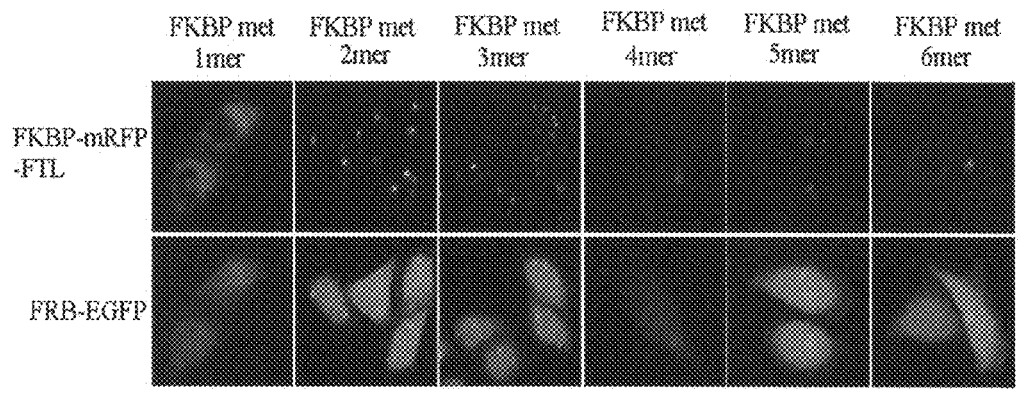

FIG. 32 is a fluorescence micrograph showing a nano-assembly matrix, obtained in the case where the number of FKBP(F36M) mutation proteins was regulated.

Figure 33:
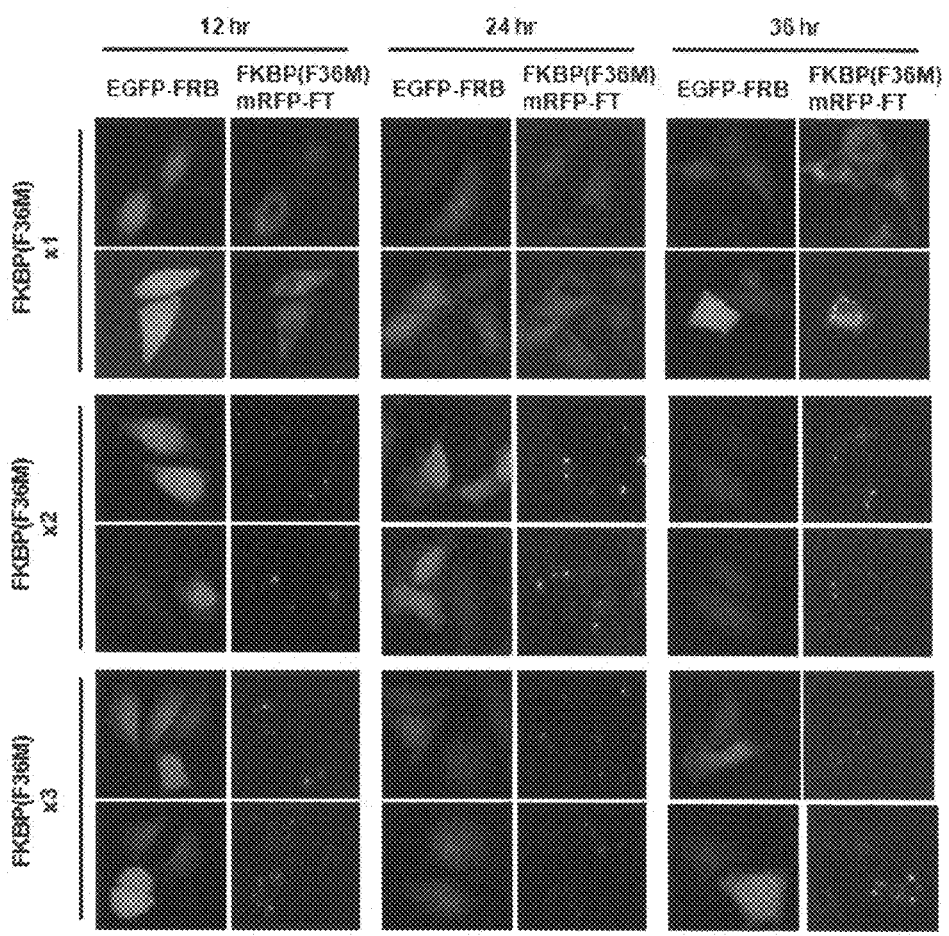

FIG. 33 is a fluorescence micrograph showing the patterns of nano-assembly matrices at varying points of time, obtained in the case where the number of FKBP(F36M) mutation proteins was regulated.

Figure 34:
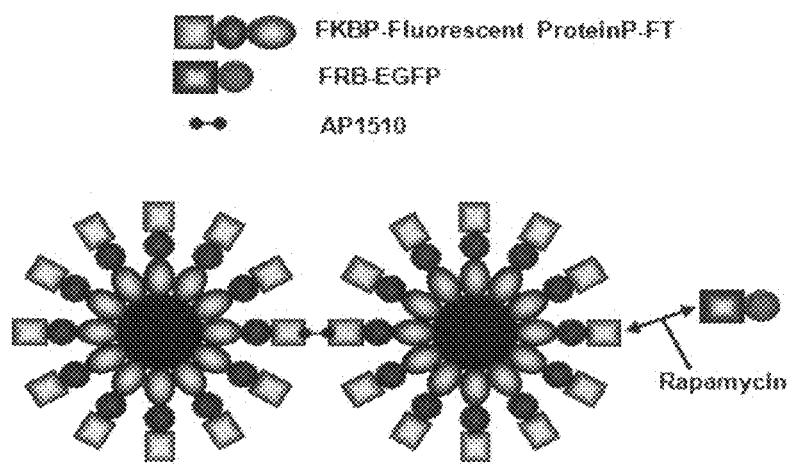

FIG. 34 is a schematic diagram showing the formation and docking of a nano-assembly matrix by FRB-FKBP interactions including treatment with AP1510 which is an FKBP interaction-mediating (regulating) compound.

Figure 35:
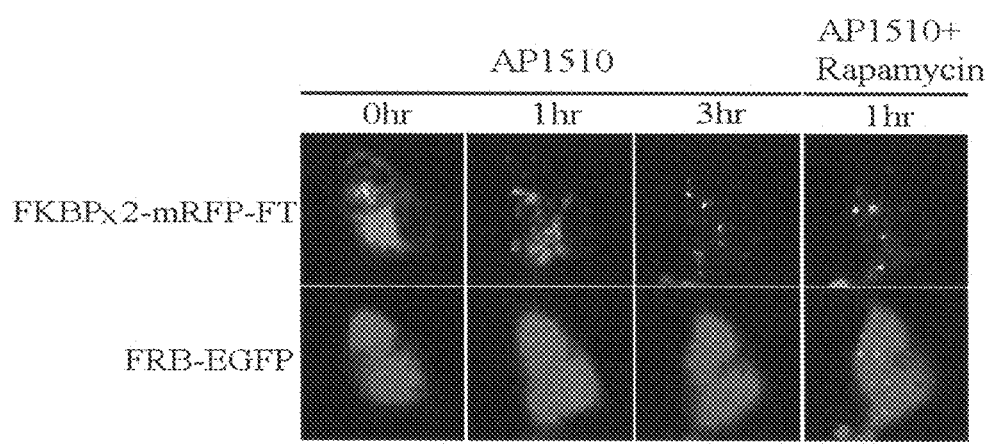
Figure 37:
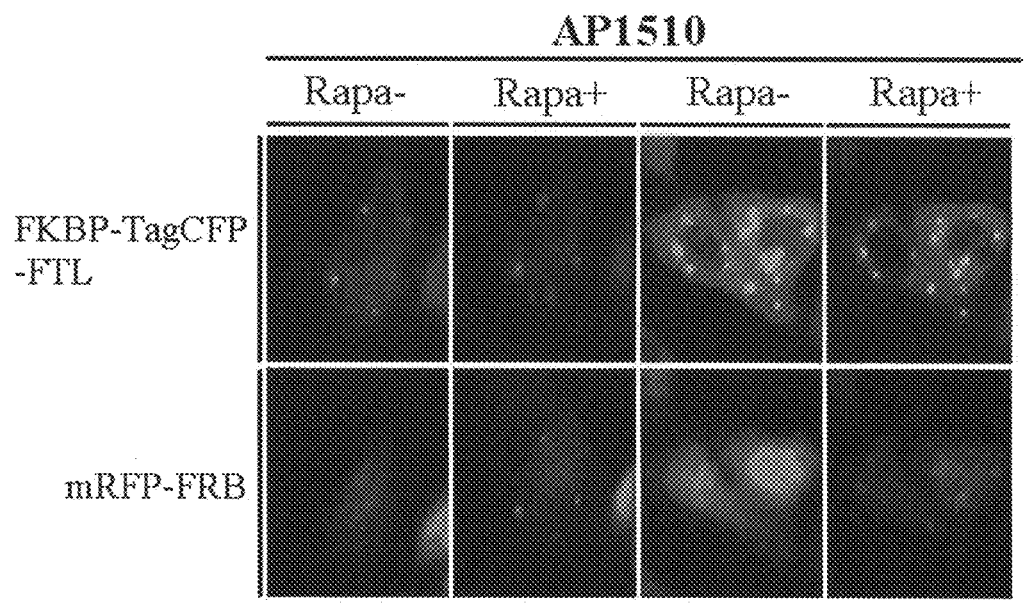

FIG. 35 and FIG. 37 are fluorescence micrographs showing the formation and docking of a nano-assembly matrix by FRB-FKBP interactions including treatment with AP1510 which is an FKBP interaction mediating (regulating) compound.

Figure 36:
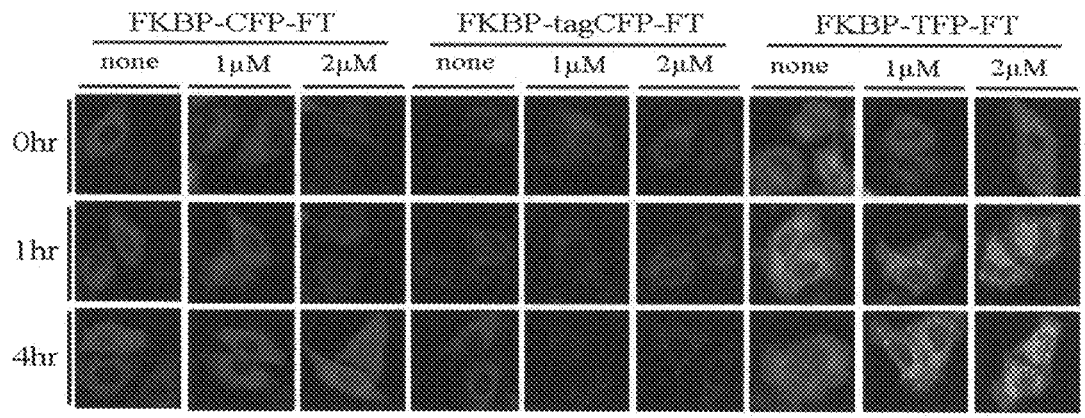

FIG. 36 is a fluorescence micrograph showing observation results for the influence of various fluorescent proteins.

DETAILED DESCRIPTION OF THE INVENTION, AND PREFERRED EMBODIMENTS

The definition of terms used in the present invention is as follows.

As used herein, the term "bioactive compound" means a compound which binds to biomolecules including proteins, nucleic acids, saccharides or lipids in vivo to regulate the function or activity of the biomolecules. Such a bioactive compound is extracted from an organism or prepared by chemical synthesis. Various antibiotics, for example, "Cyclosporine A" (Novartis AG) and "FK506" (Fujisawa), which are used to reduce immune rejection following an organ transplantation, were isolated from microorganisms, plants or marine organisms. Such a natural or synthetic bioactive compound is developed as a new drug, after it is tested for its pharmacological activity and is subjected to clinical tests using an animal model and a human model.

As used herein, the term "bioactive molecule" can be defined as a material which performs regulatory functions, such as promoting or inhibiting the function of the organism's body during the life of organisms. Such a bioactive molecule can be obtained from natural products such as animals or plants or extracted or purified from the metabolites of microbial, animal and plant cell lines. Moreover, it can also be obtained by chemical synthesis. Examples of the bioactive molecules may include nucleic acids, nucleotides, proteins, peptides, amino acids, saccharides, lipids, vitamins and chemical compounds.

As used herein, the term "bait" refers to a bioactive molecule which is used to detect interactions with other bioactive molecules.

As used herein, the term "prey" refers to a bioactive molecule to be probed (analyzed) or detected, which is an interaction partner for the "bait".

As used herein, the term "target molecule" refers to a material to be detected. According to intended use, the target molecule may be the prey, which interacts with the bait. Also, the target molecule may be a material which activates, induces, blocks or inhibits the interactions between the bait and the prey. Namely, the target molecules include all the molecules to be identified. Among them, a molecule which blocks or inhibits the interaction between the bait and the prey is defined as a "blocker molecule", and a molecule which activates or induces the interactions thereof is defined as an "activator molecule".

As used herein, the term "nano-assembly matrix" refers to a large matrix which can be readily observed by the repeated assembly or interaction of molecules. The assembly includes self-assembly. The term "nano-assembly matrix-forming material" refers to all materials having a property and function capable of forming the nano-assembly matrix.

As used herein, the term "mediator (regulator) material" refers to a material inducing the formation of the nano-assembly matrix. This is meant to include all materials capable of inducing the formation of the nano-assembly matrix through direct or indirect binding, interaction or fusion with the nano-assembly matrix-forming material. A material that mediates or regulates the activity of the mediator (regulator) material may also be defined as a mediator (regulator) material in a broad sense. The mediator (regulator) molecules include not only specific compounds or proteins, which induce the formation of the nano-assembly matrix, but also phenomena such as specific mutations, and specific physiological signals. For example, the formation of the nano-assembly matrix can be induced through the interactions between proteins resulting from physiological signals, the interactions between RNA and protein, the use of a specific mutation of a specific protein, or the use of a protein interacting only with a specific compound, and such phenomena and signals are referred to as "mediator (regulator) materials" in the specification of the present invention.

Hereinafter, the present invention will be described in detail.

In one aspect, the present invention relates to a method for detecting the interaction between a specific molecule "bait" (e.g., a specific bioactive molecule) and a molecule "prey" (e.g., another bioactive molecule) to be analyzed and detected, in vitro or in vivo.

In a first aspect, the present invention provides a method for detecting molecular interactions, comprising the steps of: (i) providing a nano-assembly matrix-forming material, a bait and a prey to the same field or system; (ii) forming a nano-assembly matrix by the interaction between the bait and the prey; and (iii) examining whether the nano-assembly matrix was formed, thus detecting the bait-prey interaction. Preferably, each of the bait and the prey can be provided in a state in which a label is bound thereto. Herein, in the step (i), a mediator (regulator) material capable of mediating or regulating the interaction between the bait and the prey may additionally be provided. The mediator (regulator) material can also be provided in a state in which a label is bound thereto.

A material capable of forming a nano-assembly matrix (hereinafter referred to as "nano-assembly matrix-forming material") can be provided in a state in which any detection material bait is bound directly or indirectly thereto, while the nano-assembly matrix-forming material is bound to another detection material prey to be analyzed. Moreover, the nano-assembly matrix-forming material can be provided in a state in which a mediator (regulator) material is bound thereto, while the bait molecule and the prey molecule can be provided in a state in which a mediator (regulator) is bound thereto.

In the method for detecting molecular interactions according to the first aspect of the present invention, when the nano-assembly matrix is formed, the bait-prey interaction or bait-prey-mediator interaction can be determined to occur, and when the nano-assembly matrix is not formed, it can be determined that such materials do not interact with each other.

Figure 1:
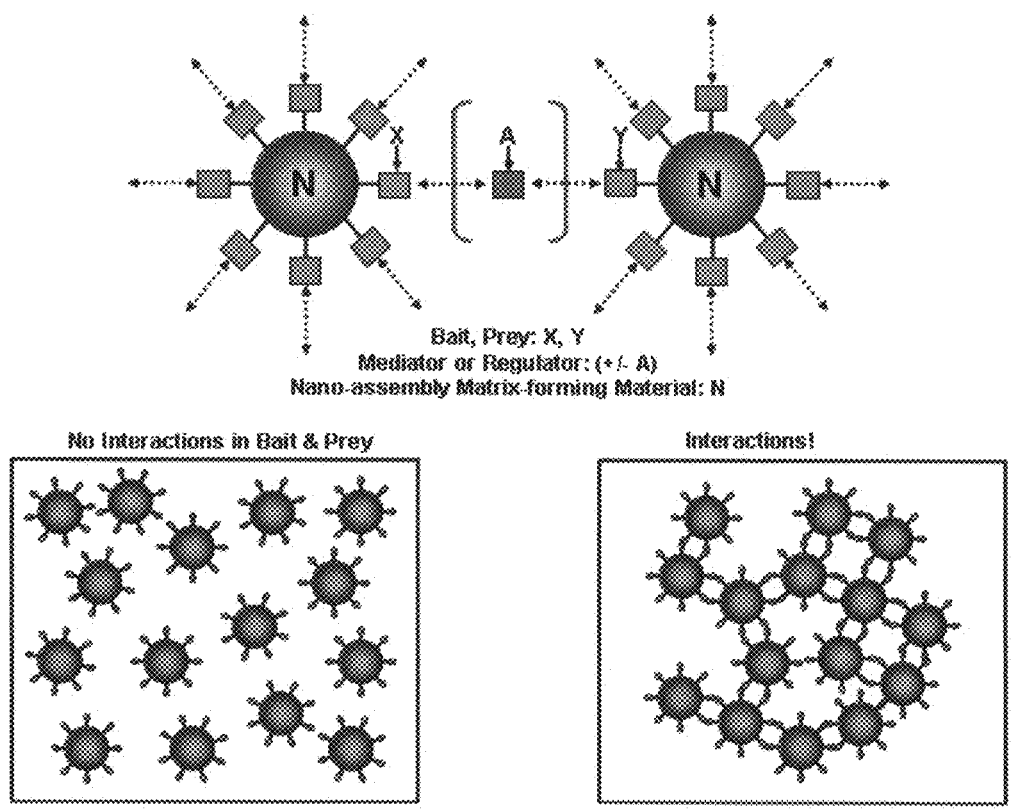
FIG. 1 is a schematic diagram showing a construct according to a first method of the present invention for detecting the direct interaction between X and Y or the indirect interaction between X and Y by A.

A schematic diagram of the first method is shown in FIG. 1. In this method, whether the nano-assembly matrix is formed by the bait-prey interaction is examined. For example, the method can be used to detect the interaction between a prey, a bait and a mediator (regulator) material, if the interactions between the materials are unknown.

Herein, the bait-prey interaction may be the direct interaction between the two molecules or may be the indirect interaction caused by a material which mediates (regulates) the interaction between the bait and the prey. In the latter case, the mediator (regulator) materials may be a combination of two or more thereof.

In one example, FIG. 4 schematically shows that detection materials FKBP (corresponding to "X" in FIG. 1) and FRB (corresponding to "Y" in FIG. 1) interact with each other by Rapamycin (corresponding to "A" in FIG. 1) to form a nano-assembly matrix by a ferritin fusion protein.

A schematic diagram of examples according to the first aspect of the present invention is shown in FIG. 15. Namely, FIG. 15 schematically shows that detection materials IkBα and RelA interact with each other in various ways (A, B and C) to form nano-assembly matrix-forming matrixes by a ferritin fusion protein.

First, "A" in FIG. 15 shows a case in which a nano-assembly matrix is formed by the direct interaction between IkBα and RelA (prey and bait), each being fused to ferritin. Also, "B" in FIG. 15 shows a case in which a large nano-assembly matrix is formed in cells by fusing bait IkBα and mediator (regulator) FRB protein to ferritin, fusing mediator (regulator) FKBP to prey RelA protein, and then causing the interaction between mediator (regulator) materials FRB and FKBP and the interaction between bait and prey molecules IkBα and RelA. "C" in FIG. 15 shows a case in which a larger nano-assembly matrix is formed by fusing only mediator (regulator) material FRB to ferritin, fusing mediator (regulator) FKBP to each of IkBα and RelA (prey and bait) and inducing the interaction between the mediator (regulator) materials FRB and FKBP to link FKBP to the FRB of ferritin.

The cases of "B" and "C" in FIG. 15 employ the indirect interaction between IkBα and RelA, and for this reason, the interaction between mediator (regulator) materials FRB and FKBP is used. Specifically, the mediator (regulator) materials FRB and FKBP and the prey-bait IkBα and RelA interact with each other to form a large nano-assembly matrix. Herein, Rapamycin which is another material mediating (regulating) the interaction between the mediator (regulator) materials FRB and FKBP may additionally be used.

Particularly, the case of "C" in FIG. 15 shows that a larger nano-assembly matrix can be formed through multiple interactions between materials by attaching only the mediator (regulator) material FRB to the ferritin protein.

In addition to the above-described method of detecting molecular interactions by detecting the formation of a nano-assembly matrix caused by the direct or indirect interactions between detection materials, the present invention provides other two detecting methods as described below. In the two methods, a nano-assembly matrix is formed by mediator (regulator) materials, and then a prey capable of interacting with a bait present on the formed nano-assembly matrix is detected.

Specifically, in a second aspect, the present invention provides a method for detecting molecular interactions, comprising the steps of: (i) providing mediator (regulator) materials and a nano-assembly matrix-forming material having a bait bound thereto, to the same field or system; (ii) forming a nano-assembly matrix by the interaction between the mediator materials; (iii) providing a prey to the formed nano-assembly matrix; and (iv) measuring the binding location of the prey by interaction with the bait present on the formed nano-assembly matrix so as to determine whether the prey co-localizes with the bait, thus detecting the prey-bait molecular interaction (see the upper figure of FIG. 2).

In a third aspect, the present invention provides a method for detecting molecular interactions, comprising the steps of: (i) providing a nano-assembly matrix-forming material having first mediator (regulator) materials bound thereto, and a bait having second mediator (regulator) molecules bound thereto, to the same field or system; (ii) forming a nano-assembly matrix by the interactions between the first mediator (regulator) materials and binding the bait to the formed nano-assembly matrix by the interaction between the second mediator materials; (iii) providing a prey to the formed nano-assembly matrix; and (iv) measuring the binding location of the prey by the interaction with the bait bound to the formed nano-assembly matrix so as to determine whether the prey co-localizes with the bait, thus detecting the bait-prey molecular interaction (see the lower figure of FIG. 2).

In step (ii) of each of the methods according to the second and third aspects, another mediator (regulator) material which interacts with the mediator (regulator) materials to induce the formation of the nano-assembly matrix may additionally be provided. In step (iv), a material which mediates or regulates the interaction between the bait and the prey may additionally be provided. Preferably, each of the bait, the prey and the mediator (regulator) material can be provided in a state in which a label is bound thereto.

The second and third methods commonly comprise forming a nano-assembly matrix through the interaction between mediator (regulator) materials known to interact with each other, and then detecting a prey which is a partner molecule capable of interacting with the bait present on the formed nano-assembly matrix.

However, the biggest difference between the second method and third method of the present invention is that, in the step of forming the nano-assembly matrix by the interaction between the mediator (regulator) materials in the second method, the bait bound to the nano-assembly matrix-forming material participates in the formation of the nano-assembly matrix by the interaction between the mediator (regulator) materials, whereas, in the third method, the nano-assembly matrix is formed only with the nano-assembly matrix-forming material and the mediator (regulator) molecules (first mediator (regulator) molecules), and then another mediator molecules (second mediator (regulator) molecules are bound to the resulting material. Herein, a material that mediates or regulates the interactions of the first mediator (regulator) molecules or the second mediator (regulator) molecules may additionally be used.

In the second or third method for detecting molecular interactions, when it is determined that the prey co-localizes with the bait, the bait and the prey can be determined to interact with each other, and when it is determined that the prey does not co-localize with the bait, the bait and the prey can be determined not to interact with each other.

A schematic diagram of the second method of the present invention is shown in FIG. 2.

One example of the present invention will be described with reference to FIG. 2. FIG. 30 schematically shows experimental results obtained by: binding bait DHFR (corresponding to "X" of FIG. 2) to a nano-assembly matrix-forming material, ferritin protein (corresponding to "N" of FIG. 2); making a specific mutation (corresponding to "C" of FIG. 2) in FKBP proteins (corresponding to "A" and "B" of FIG. 2) present as a monomer spreading in cells so as to allow the FKBP proteins to bind to each other, thus inducing the spontaneous formation of nano-assembly matrices; and then allowing an MTX compound (corresponding to "Y" of FIG. 2) to interact with the DHFR, such that the MTX compound is docked or recruited to the nano-assembly matrices.

In another example of the second method, FIG. 34 schematically shows an experimental process comprising: binding bait FKBP (corresponding to "A", "B" and "X" of FIG. 2) to a nano-assembly matrix-forming material, ferritin protein (corresponding to "N" of FIG. 2); forming a nano-assembly matrix by a mediator (regulator) material AP1510 (corresponding to "C" of FIG. 2); and then allowing the FKBP (bait) present on the nano-assembly matrix to interact with FRB (prey) (corresponding to "Y" of FIG. 2), such that the FRB (prey) is docked or recruited to the nano-assembly matrix, whereby FKBP (bait) and FRB (prey) co-localize with each other. Herein, FKBP functions as a mediator (regulator) material of forming the nano-assembly matrix by interaction with the AP1510 compound and, at the same time, functions as a bait which interacts with FRB (prey).

A schematic diagram of the third method of the present invention is shown in the lower figure of FIG. 2.

Referring to the lower figure of FIG. 2, an example of the third method of the present invention comprises: binding a first mediator (regulator) material FKBP (A, B and D) to a nano-assembly matrix-forming material, ferritin protein (N); forming a nano-assembly matrix by the interaction between the first mediator material FKBP with an AP1510 compound (C); allowing the resulting material to interact with a specific bait (X) having a second mediator (regulator) material FRB (E) bound thereto; and binding the bait to the nano-assembly matrix by Rapamycin (F) regulating the action of the second mediator (regulator) material (FKBP-FRB interaction). Also, a prey (Y) which is a partner material for the bait (X) interacts with the bait present on the nano-assembly matrix, such that it is docked or recruited to the nano-assembly matrix, whereby the FKBP (bait) and the FRB (prey) co-localize with each other.

Herein, the second mediator (regulator) material can also be transferred to the formed nano-assembly matrix by direct interaction with the first mediator (regulator) material bound to the nano-assembly matrix-forming material, without using a separate additional mediator (regulator) molecule (i.e., without using the material F).

In the above-described methods of the present invention, the binding between the materials used in the present invention, including nano-assembly matrix-forming materials, mediator (regulator) materials inducing nano-assembly matrix formation, baits, preys and labels, may include physical, chemical, electrostatic or biological direct or indirect binding. Among them, when biological binding occurs, a probe comprising an antibody, a protein, a protein domain, a motif, a peptide and the like may be used.

Hereinafter, specific constructional elements which are used in the above-described methods will be described.

As used herein, the "nano-assembly matrix-forming materials" are materials having a plurality of the same or different binding moieties and can form matrices by the interaction or self-assembly between them. Preferably, materials that can form matrices by self-assembly are used. These matrices preferably consist of nano-sized particles.

Preferred examples of materials that form nano-assembly matrices by self-assembly may include ferritin, ferritin-like protein, magnetosome protein or viral protein. Moreover, a variety of chemically synthesized nanoparticles can also form nano-assembly matrices. For example, various kinds of nanoparticles, including gold nanoparticles, Q dots or magnetic nanoparticles, may be used. In one Example of the present invention, among molecules or proteins that can form nano-sized unit matrices by self-assembly, the ferritin protein was used.

The ferritin protein forms a spherical nanoparticle matrix by self-assembly of 24 ferririn proteins, has an outer diameter of about 12 nm and an inner diameter of about 9 nm and contains more than 2500 iron atoms (Chasteen, N. D. Struc. Biol. 126:182-194, 1999). If a nano-assembly matrix is formed by the interaction between the bait and the prey or between the mediator (regulator) materials, which occurs on the surface of the nanoparticle matrix formed by the ferritin protein, the interaction can be dynamically detected by analyzing a label, such as a fluorescent, luminescent, magnetic or radioactive material bound to the bait, the prey or the mediator (regulator) material, using an analytical device such as a microscope.

FIG. 3 shows that a nanoparticle matrix having an inner diameter of 8 nm was formed by self-assembly of 24 ferritin proteins. In FIG. 3, green beads show amino terminal portions to which various materials to be analyzed in an example of the present invention were bound. When the materials bound to the surface of the ferritin nano-matrices interact with each other, they are linked to each other in a matrix form to form a nano-assembly matrix, as observed in Example of the present invention.

The magnetosome protein is a protein present in the membrane of about 100-nm magnetic particles accumulated in the organelle magnetosome of magnetic bacteria which accumulate magnets in cells. Such magnetosome proteins may also be used in the present invention, because they can form nanoparticle matrices by self-assembly through magnetic properties therebetween.

As the bait corresponding to a detection material and the prey corresponding to the partner of the bait, any candidate molecules anticipated to interact with each other may be used. Preferably, bioactive molecules are used.

The bioactive molecules include all the materials showing physiological activity in vivo, and as the bioactive molecules, any molecules which can interact with biomaterials in vivo to regulate the function or activity of the biomaterials may be used. Preferred examples of the bioactive materials include nucleic acids, mono-/oligo-/poly-nucleotides, proteins, mono-/oligo-/poly-peptides, amino acids, mono-/oligo-/poly-saccharides, lipids, vitamins and chemical compounds and furthermore, smaller molecules constituting said molecules.

Specific examples of the interaction between the bait and the prey may include the interaction between FRB and FKBP, which are the pharmaceutically relevant binding partners of a Rapamycin compound, the interaction between an FK506 compound and an FKBP protein which is the pharmaceutically relevant partner thereof, the interaction between an AP1510 compound and an FKBP protein, the interaction between an IkBα protein and an RelA which is the binding partner thereof, the interaction between an IkBα protein, which is regulated according to a physiological signal of TNFa, and a bTrCP or IKKb protein which is the binding partner of the IkBα protein, the intracellular interaction (let-7b miRNA binding to lin-28 mRNA) of miRNA with mRNA, the interaction of an Ago2 proteion with miRNA, the interaction of an MS2 protein with an MS2-binding mRNA site, the intracellular interaction of a DHFR protein with an MTX compound, etc.

The mediator (regulator) materials which regulate the bait-prey interaction are materials that activate the bait-prey interaction to mediate (regulate) the binding between the bait and the prey, and as the mediator (regulator) materials, any bioactive molecules or compounds may be used without limitation, as long as they exhibit the above function. However, molecules interacting specifically with the bait-prey pair are preferably used. Because the nano-assembly matrix is formed by the interaction of the bait and the prey, the materials that mediate the bait-prey interaction are considered to belong to the range of the mediator (regulator) materials which induce the formation of nano-assembly matrices as defined in the present invention.

To mediate (regulate) the prey-bait interaction, a protein which is regulated by an external signal may be used. Alternatively, the property of miRNA specifically binding to the target mRNA may also be used. In one example, FIG. 22 schematically shows that a large nano-assembly matrix is formed by a ferritin fusion protein according to the interaction between RNA and a regulator protein. Particularly, the use of a protein which is regulated according to an external signal makes it possible to analyze the interaction between very sensitive detection materials, which occurs in cells by physiological signals.

In one Example of the present invention, when an FKBP-FRB pair was used, Rapamycin was used as a mediator (regulator) material, and when an IkBα-bTrCP pair and an IkBα-IKKb pair were used, TNFa which is regulated according to an external signal was used a mediator (regulator) material. In addition, when a PAZ-MS2CP pair was used, the binding between let-7b(miRNA) and lin28-MS2bs(mRNA) was used as a mediator (regulator) material.

The mediator (regulator) materials which induce the formation of nano-assembly matrices in the present invention are meant to include all materials which can interact directly or indirectly with each other on the surface of the nano-assembly matrix-forming materials to form nano-assembly matrices. Such materials that mediate or regulate the activity of the mediator (regulator) materials are also considered as mediator (regulator) materials in a broad sense. When the formation of nano-assembly matrices is induced by the bait-prey interaction as described above (first method), materials that regulate or mediate the bait-prey interaction are also included in the range of said mediator (regulator) materials in a broad sense.

As such mediator (regulator) materials, any materials may be used without limitation, as long as they exhibit the function of inducing the formation of nano-assembly matrices. Accordingly, all the materials or phenomena that can induce the formation of nano-assembly matrices by specific phenomena, such as either the binding between materials interacting specifically with each other or mutations can be understood as mediator (regulator) materials. Namely, the term "mediator (regulator) materials" as used herein is meant to include all specific materials, specific phenomena or specific interactions. Such mediator (regulator) materials may be used in a combination of two or more thereof.

If the prey was detected using the properties of the bait-prey pair, while a nano-assembly matrix was formed using the properties of the bait, it is considered that the used bait is a mediator (regulator) material inducing the formation of the nano-assembly matrix and, at the same time, exhibits the function of the bait used to detect an interaction with the partner prey.

In one example, FKBP proteins induce the formation of nano-assembly matrices by binding with each other through specific mutations, and then an FRB protein is docked or recruited to the nano-assembly matrices by the interaction between the FKBP protein and the partner protein FRB through Rapamycin (FIG. 27). In this case, the FKBP protein exhibits a function of forming nano-assembly matrixes by mutations (function as a mediator (regulator) material) and, at the same time, exhibits a function of interacting with the FRB protein (function as a bait). In addition, Rapamycin that mediates (regulates) the FRB-FKBP interaction also corresponds to another mediator (regulator) material [Example 6-(1)].

In another example, the formation of nano-assembly matrices is induced by attaching a FKBP protein to ferritin and treating the protein with AP1510 (a compound which mediates (regulates) the FKBP interaction), and then the FRB protein, which is the partner material for FKBP, is bound and docked or recruited to the surface of the nano-assembly matrices by the interaction between the FKBP and FRB proteins through Rapamycin. In this case, the FKBP protein simultaneously exhibits a function of forming the nano-assembly matrix by AP1510 (function as a mediator (regulator) material) and a function of interacting with the FRB protein (function as a bait). Likewise, Rapamycin that mediates (regulates) the FRB-FKBP interaction also corresponds to another mediator (regulator) material [Example 7].

Meanwhile, in the methods of the present invention, it is preferable to use a label to examine the prey-bait interaction. Particularly, the bait, the prey and/or the mediator (regulator) material is more preferably used in a state in which a label is bound thereto.

The interaction between the bait and the prey can be dynamically detected by measuring whether the prey to be detected and the bait co-localize with each other on the nano-assembly matrix formed by the interaction between the specific materials, using the label.

As the label in the present invention, a radioactive label, a fluorescent material or a luminescent material may be used. As the radioactive label, all the generally usable labels, for example, $^{32}P$, $^{35}S$, $^{3}H$ and $^{14}C$, may be used. Examples of the fluorescent material which shows fluorescence by itself or shows fluorescence by the interaction between molecules may include: fluorescent dyes, such as FITC and rhodamine; fluorescent proteins, such as ECFP, TagCFP, mTFP1, GFP, YFP, CFP and RFP; tetracystein motifs; and fluorescent nanoparticles. As the luminescent material, a luminescent material which emits luminescence by itself or shows luminescence by interactions between molecules may be used. For example, luciferase may be used as the luminescent material.

In the present invention, the change of the location or motion of labels can be measured using generally widely known methods, such as optical means including a microscope, a scanner, a radioactive label detecting device, a fluorescence polarization reader (FP reader), a spectrophotometer, MRI (magnetic resonance imaging), SQUID, a fluorescence detector, a luminescence detector, etc.

In the method according to the first aspect of the present invention as described above, molecular interactions are detected through the formation of nano-assembly matrices by the bait-prey interaction. Herein, the nano-assembly matrix may also be formed through the direct binding between the bait and the prey, which are bound to the nano-assembly matrix-forming materials, but the bait and the prey may also be bound indirectly to each other through another mediator (regulator) material which interacts with each of the bait and the prey (FIG. 1). Namely, in the first method, whether the nano-assembly matrix was formed is determined by the bait-prey interaction.

In the methods according to the second and third aspects of the present invention, the formation of the nano-assembly matrix by the nano-assembly matrix-forming material is performed using a mediator (regulator) material (a material inducing the formation of the nano-assembly matrix). Herein, the nano-assembly matrix-forming material is either provided in a state in which it is bound to the mediator (regulator) material and the bait (second method) or provided in a state in which it is bound only to the mediator (regulator) material (third method). In the latter case, the bait is provided separately without being bound to the nano-assembly matrix-forming material, but it is preferably provided in a state in which it is fused with a mediator (regulator) material which enables it to be transferred onto the formed nano-assembly matrix. In the present invention, for the convenience of description, mediator (regulator) materials which are involved in the formation of nano-assembly matrices are referred to as first mediator (regulator) materials, while mediator (regulator) materials which enable the bait to be transferred are referred to as second mediator (regulator) materials.

According to the second and third methods of the present invention, a nano-assembly matrix is formed by mediator (regulator) materials, and the bait is bound directly to the nano-assembly matrix or is present on a portion of the formed nano-assembly matrix by mediator (regulator) materials.

Thus, when the bait which is present on the formed nano-assembly matrix interacts with the partner prey, both the prey and the bait co-localize with each other, and when the bait does not interact with the prey, they do not co-localize. In other words, in the second and third aspects of the present invention, the prey is not involved directly in the formation of the nano-assembly matrix, and the measurement of the location of the prey by docking or recruitment to the formed nano-assembly matrix is considered to be the standard for detecting molecular interactions. The docking or recruitment of the prey is achieved by interaction with the bait present on the formed nano-assembly matrix.

"The co-localization of the prey and the bait on the nano-assembly matrix" does not means a state in which the bait and the prey are bound to each other in order to form the nano-assembly matrix, but means a state in which the bait, which locates at separate sites other than binding moieties forming the nano-assembly matrix, and the prey introduced as a second construct, are bound to each other by interaction, and thus co-localize on the same nano-assembly matrix.

Accordingly, in the second and third methods, the formation of the nano-assembly matrix is induced by mediator (regulator) materials, and the interaction between the bait and the prey determines that the prey co-localizes with the bait of the nano-assembly matrix. Therefore, if the prey does not interact with the bait, the prey is maintained at other locations, such as a homogenous state, during the formation of the nano-assembly matrix.

In the first, second and third methods of the present invention, static results can be obtained after completion of the bait-prey binding interaction or the interaction of mediator (regulator) materials, and the process of forming the nano-assembly matrix by mediator (regulator) materials can be dynamically observed even before completion of the interaction. Particularly in the second and third methods, the dynamic analysis of co-localization is possible. Such a dynamic analysis method is advantageous in that the signal-to-ratio can be increased.

The method of the present invention can be carried out in vitro or in vivo. If the method of the present invention is carried out in vivo, it can be carried out: in prokaryotes or eukaryotes; in organs, tissues or cells of mammals; and in organs, tissues or cells of plants. Particularly, the method of the present invention can be carried out in organs, tissues or cells of Zebra fish, C. elegans, yeast, flies or frogs.

The nano-assembly matrix-forming materials, the baits, the preys, the mediator (regulator) materials (materials inducing the formation of nano-assembly matrices) and the labels, which are used in the present invention, can be introduced into cells through generally widely known methods. For example, they can be introduced into cells by the use of transducible peptide (or fusogenic peptide), lipid (or liposome) gene transporter or the binding complex thereof; or by incubating them with cells in OPTI-MEM; or by electroporation or magnetofection. In particular, when the method of the present invention is carried out in vivo, it can be carried out within living cells on a culture plate/dish or within microarrayed living cells.

In order to use said method to detect a specific prey interacting with a specific bait, preys can be provided as a library.

Specifically, according to the first method of the present invention, there is provided a method for detecting a target prey interacting with a bait, the method comprising the steps of: (i) providing nano-assembly matrix-forming materials and libraries of baits and preys to the same field or system; (ii) forming nano-assembly matrices by the interactions between the bait library and the prey library; (iii) examining whether the nano-assembly matrices were formed, thus detecting the interaction between the bait and the prey; and (iv) selecting, isolating and identifying a target prey, which interacts with the bait to form nano-assembly matrices.

According to the second method of the present invention, there is provided a method for detecting a target prey interacting with a bait, the method comprising the steps of: (i) providing mediator (regulator) materials and nano-assembly matrix-forming materials having a bait bound thereto, to the same field or system; (ii) forming nano-assembly matrices by the interaction between the mediator (regulator) materials; (iii) providing a prey library to the formed nano-assembly matrices; (iv) measuring the binding location of the prey by interaction with the bait present on the formed nano-assembly matrices so as to determine whether the prey co-localizes with the bait, thus detecting the interactions; and (v) selecting, isolating and identifying a target prey, which interacts with the bait to co-localize with the bait on the nano-assembly matrices.

According to the third method of the present invention, there is provided a method for detecting a target prey interacting with a bait the method comprising the steps of: (i) providing nano-assembly matrix-forming materials having first mediator (regulator) materials bound thereto, and a bait having second mediator (regulator) materials bound thereto, to the same field or system; (ii) forming nano-assembly matrices by the interaction between the first mediator (regulator) materials and binding the bait to the formed nano-assembly matrices by the interaction between the second mediator (regulator) materials; (iii) providing a prey library to the formed nano-assembly matrices; (iv) measuring the binding location of the preys by interaction with the bait present on the formed nano-assembly matrices so as to determine whether the prey co-localizes with the bait, thus detecting the interactions; and (v) selecting, isolating and identifying a target prey, which interacts with the bait to co-localize with the bait on the nano-assembly matrices.

The detailed description of each of the methods is the same as described above. Using the above methods, preys which interact with baits to co-localize on nano-assembly matrices can be selected, isolated and identified as target molecules.

Also, the present invention provides a method of detecting the interaction between a bait and a prey and analyzing and detecting a third molecule target molecule influencing the interaction.

Specifically, according to the first method of the present invention, there is provided a method for detecting a target molecule which blocks (inhibits) or activates (induces) the interaction between a bait and a prey, the method comprising the steps of: (i) providing mediator (regulator) materials and nano-assembly matrix-forming materials having a bait bound thereto, to the same field or system; (ii) forming nano-assembly matrices by the interaction between the mediator (regulator) materials in the presence of target candidates; (iii) providing a prey to the formed nano-assembly matrices; and (iv) selecting, as a target blocker molecule or a target activator molecule, a target candidate corresponding to a case in which the degree of co-localization of the bait with the prey in the presence of the target candidate is blocked (inhibited) or activated (induced) compared to the degree of co-localization of the bait with the prey in the absence of the target candidate.

According to the second method of the present invention, there is provided a method for detecting a target molecule which blocks (inhibits) or activates (induces) the interaction between a bait and a prey, the method comprising the steps of: (i) binding mediator (regulator) materials and a bait to nano-assembly matrix-forming materials and providing these materials to the same field or system; (ii) forming nano-assembly matrices by the interactions between the mediator (regulator) materials in the presence of target candidates; (iii) providing a prey to the formed nano-assembly matrices; (iv) selecting, as a target blocker molecule or a target activator molecule, a target candidate corresponding to a case in which the degree of co-localization of the bait with the prey in the presence of the target candidate is blocked (inhibited) or activated (induced) compared to the degree of co-localization of the bait with the prey in the absence of the target candidate.

According to the third method of the present invention, there is provided a method for detecting a target molecule which blocks (inhibits) or activates (induces) the interaction between a bait and a prey, the method comprising the steps of: (i) providing nano-assembly matrix-forming materials having first mediator (regulator) materials bound thereto, and a bait having second mediator (regulator) materials bound thereto, to the same field or system; (ii) forming nano-assembly matrices by the interaction between the first mediator (regulator) materials in the presence of target candidates, and binding the bait to the formed nano-assembly matrices by the interaction between the second mediator (regulator) materials; (iii) providing a prey to the formed nano-assembly matrices; and (iv) selecting, as a target blocker molecule or a target activator molecule, a target candidate corresponding to a case in which the degree of co-localization of the bait with the prey in the presence of the target candidate is blocked (inhibited) or activated (induced) compared to the degree of co-localization of the bait with the prey in the absence of the target candidate.

The detailed description of each of the above methods is the same as described above. Using the above-described methods, a target candidate, which influences the interaction between a bait and a prey, that is, blocks (inhibits) or activates (induces) the interaction between a bait and a prey, can be detected.

EXAMPLES

Hereinafter, the present invention will be described in further detail with reference to examples. It is to be understood, however, that these examples are for illustrative purposes only and are not to be construed to limit the scope of the present invention.

Example 1

Formation of Nano-Assembly Matrices by Interaction Between Compound (Rapamycin) and Proteins (FKBP and FRB)

Ferritin gene FTH1 (GenBank BC013724) and FTL (GenBank BC016346) were purchased from Open BioSystems, Inc., USA.

In the present invention, various proteins were attached to the end of ferritin protein and used in analysis. pcDNA 3.1-based recombinant genes were prepared, which can express various fusion proteins, obtained by attaching various detection proteins (e.g., FKBP and FRB) and fluorescent proteins (e.g., mRFP, EGFP, ECFP and YFP) to the amino terminal ends of ferritin protein (FT), in mammalian cells by a CMV promoter.

The recombinant gene FKBP-mRFP-FT and FRB-mRFP-FT were introduced alone or together into previously cultured Hela cells (ATCC No. CCL-2) using electroporation (1000 V, 35 ms, 2 pulses). Then, the cells were plated in a 16-well chamber slide (Nunc) and cultured in a 5% $CO_2$ incubator at 37° C. for 24 hours to express the fusion protein. For imaging, 10% FBS-containing DMEM (Gibco) was replaced with OPTI-MEM (Gibco), and then the cells were treated with 250 nM (stock concentration: 1 mM of stock; dissolved in DMSO) of Rapamycin (Calbiochem), and the distribution of the ferritin fusion protein in the cells was observed with a fluorescent microscope (Olympus, IX51) (FIG. 5).

FIG. 4 schematically shows this Example in which a nano-assembly matrix was formed through the indirect interaction between the detection molecules FKBP and FRB by the mediator material Rapamycin, and results of this Example are shown in FIG. 5.

As a negative control group, cells in which only one of the recombinant genes FKBP-mRFP-FT and FRB-mRFP-FT was expressed were used. In these cells, a nano-assembly matrix was not formed in all the cases where the cells were treated and not treated with Rapamycin. However, in the case where the proteins of FKBP-mRFP-FT and FRB-mRFP-FT were expressed in a cell, a nano-assembly matrix was formed in the cell, only when the cell was treated with Rapamycin.

Namely, the detection molecules FKBP and FRB bound to the ferritin protein were cross-linked by the mediator (regulator) material Rapamycin which interacted with them, thus forming a nano-assembly matrix in the cell.

(1) Formation of Nano-Assembly Matrix with the Passage of Time

The interaction between FKBP, Rapamycin and FRB was observed in real time in order to observe a mode in which a nano-assembly matrix of ferritin is formed.

The recombinant genes FKBP-EGFP-FT and FRB-mRFP-FT were introduced together into cultured Hela cells, and then the ferritin fusion proteins were expressed in the cells. Then, the cells were treated with 250 nM of Rapamycin, and the distribution of the ferritin fusion protein in the cells was analyzed with a fluorescence microscope at 2-minute intervals for 10 minutes.

As a result, as can be seen in FIG. 6, in the case where the FKBP-EGFP-FT and FRB-mRFP-FT proteins were expressed together in the cells, the proteins rapidly interacted with each other by treatment with Rapamycin, and the nano-assembly matrix was formed in the cells within 10 minutes.

(2) Formation of Nano-Assembly Matrix Regardless of Fluorescent Protein

To support the fact that a nano-assembly matrix of ferritin is produced dependent upon treatment with Rapamycin, recombinant genes FKBP-mRFP-FT and FRB-EGFP-FT, prepared by exchanging fluorescent proteins from the pairs of FIG. 6 were introduced into cultured Hela cells, and then the ferritin fusion proteins were expressed in the cells. Then, the cells treated with 250 nM of Rapamycin and the cells not treated with Rapamycin were observed with a fluorescence microscope for 10 minutes.

As a result, as shown in FIG. 7, in the case where the FKBP-mRFP-FT and FRB-EGFP-FT proteins were expressed together in the cells, the proteins rapidly interacted with each other to form a nano-assembly matrix, only when the cells were treated with Rapamycin.

(3) Formation of Nano-Assembly Matrix by Specific Interaction

To show the fact that a nano-assembly matrix of ferritin is formed by the specific interaction between FKBP, Rapamycin and FRB, a ferritin fusion protein as a combination of FKBP-EGFP-FT with mRFP-FT, prepared by removing FRB, was expressed in Hela cells. Then, the cells were treated with 250 nM of Rapamycin.

As a result, as shown in FIG. 8, unlike the results of FIGS. 6 and 7, only FKBP was expressed as a ferritin fusion protein, and thus the specific interaction between FKBP and FRB by Rapamycin did not occur, suggesting that no nano-assembly matrix was formed in the cells.

Also, according to the above method, a ferritin fusion protein as a combination of FRB-mRFP-FT with EGFP-FT, prepared by removing FKBP, was expressed in Hela cells, and the cells were treated with Rapamycin. As a result, as shown in FIG. 9, only FRB was expressed as a ferritin fusion protein, and thus no nano-assembly matrix was formed in the cells.

Such results indicate that a high-assembly matrix of ferritin was formed through the specific interaction between FKBP and FRB by Rapamycin.

(4) Formation of Nano-Assembly Matrix in Stem Cells

The recombinant genes FKBP-mRFP-FT and FRB-EGFP-FT were introduced together into human mesenchymal stem cells derived from human bone marrow, and then the ferritin fusion protein was expressed in the cells. Then, the cells were treated with 250 nM of Rapamycin (Calbiochem), and the distribution of the ferritin fusion protein in the cells was analyzed with a fluorescence microscope.

As a result, as shown in FIG. 10, in the case where the FKBP-mRFP-FT and FRB-EGFP-FT proteins were expressed together in the cells, FKBP and FRB interacted with each other to form a nano-assembly matrix in the stem cells.

Test Example 1-1

Whether Formation of Nano-Assembly Matrix Depends on Mediator (Regulator) Materials As shown in FIG. 11, in order to verify the specificity of Rapamycin-mediated formation of a nano-assembly matrix, FK506, which binds specifically only to the FKBP protein and does not bind to the FRB protein, was used as a competitive compound for Rapamycin, and cells were treated with the competitive compound.

Specifically, cells were treated with 25 µM of FK506 for 10 minutes, and then 250 nM of Rapamycin was added to the cells. In this case, because FK506 interfered with the binding between Rapamycin and FKBP, a nano-assembly matrix formed through the interaction between the FKBP and FRB proteins by Rapamycin could not be observed, unlike the results of FIGS. 6 and 7.

Test Example 1-2

Whether Formation of Nano-Assembly Matrix Depends on Fluorescent Material

In a combination of FKBP-EGFP-FT with FRB-ECFP-FT and a combination of FKBP-YFP-FT with FRB-mRFP-FT in addition to a combination of FKBP-mRFP-FT with FRB-mRFT-FT (FIG. 5) or a combination of FKBP-mRFP-FT with FRB-EGFP-FT (FIGS. 6 and 7), when cells were treated with 250 nM of Rapamycin, the FKBP and FRB proteins efficiently interacted specifically with each other within 10 minutes to form a nano-assembly matrix.

Namely, it was found that the nano-assembly matrix formed through the interaction between the FKBP and FRB proteins by Rapamycin was not influenced even when other various fluorescent proteins were attached to the ferritin protein (FIG. 12 and FIG. 13).

Test Example 1-3

Whether Formation of Nano-Assembly Matrix Depends on Place

Because ferritin is a protein which locates in the cytoplasm, the interaction between the FKBP and FRB proteins by Rapamycin was observed mainly in the cytoplasm.

In order to examine whether molecular interactions in various organelles in cells can be seen through the formation of a nano-assembly matrix of ferritin, NLS (nuclear localization signal) was attached to the ferritin protein, such that the ferritin fusion protein could be translocated into nuclei. In this state, the cells were treated with 250 nM of Rapamycin. As a result, it was observed that a nano-assembly matrix could be formed in nuclei by the interaction between the FKBP and FRB proteins, even though the efficiency of the formation was low compared to the case of formation in the cytoplasm (FIG. 14).

Example 2

Formation of Nano-Assembly Matrix by Interaction Between Proteins

Whether a nano-assembly matrix is formed by the interaction between detection molecules IkBα and RelA in various ways (A, B and C) as shown in FIG. 15 was examined.

(1) Method of "A" in FIG. 15

A test was carried out in order to examine a nano-assembly matrix can be spontaneously formed in cells through the expression of IkBα and RelA, when IkBα and RelA are fused directly to the ferritin protein.

The recombinant genes IkBα-YFP-FT (pcDNA 3.1) and RelA-mRFP-FT (pcDNA 3.1) were introduced into the Hela cells cultured in Example 1, and then the ferritin fusion protein was expressed in the cells. As a result, as shown in FIG. 16, a nano-assembly matrix was formed in the cells through the interaction between the IkBα and RelA proteins.

(2) Method of "B" in FIG. 15

Each of the IkBα and FRB proteins was fused to ferritin, and the RelA protein was fused with FKBP. The fusion proteins were treated with 250 nM of Rapamycin. Namely, for the mediator (regulator) materials (FRB-FKBP), Rapamycin was used as another mediator (regulator) material for regulating the interaction between the mediator (regulator) materials.

The recombinant genes FRB-ECFP-FT, FKBP-mRFP-RelA and IkBα-YFP-FT were introduced together into Hela cells, and then the ferritin fusion protein was expressed in the cells. As a result, as shown in FIG. 17, it was observe that, as the cells were treated with Rapamycin, the FRB and FKBP proteins as the mediator (regulator) materials interacted with each other, while the IkBα and RelA protein as the prey and bait interacted with each other, thus forming a large nano-assembly matrix in the cells.

(3) Method of "C" in FIG. 15

The FKBP protin was fused to IkBα and RelA, and only FRB was fused to ferritin. A test was carried out to observe whether the FKBP protein in IkBα and RelA can be linked with FRB of ferritin through Rapamycin to form a nano-assembly matrix. The recombinant genes FRB-ECFP-FT, FKBP-mRFP-RelA and IkBα-YFP-FKBP were introduced together into Hela cells, and then each of the fusion proteins was expressed in the cells. As a result, as shown in FIG. 18, it was observed that, as the cells were treated with Rapamycin, the FRB and FKBP proteins as the mediator (regulator) materials interacted with each other, while the IkBα and RelA proteins interacted with each other, thus forming a large nano-assembly matrix in the cells.

Namely, it was found that, when only the mediator (regulator) material FRB was attached to the ferritin protein, a larger nano-assembly matrix could be formed through multiple interactions between detection molecules, unlike the results of the experiment (2).

From such results, it could be seen that a nano-assembly matrix was formed in cells through the interaction between detection molecules, like lego, in various flexibilities, and thus the interaction between detection molecules could be analyzed in various flexibilities.

(4) Different Combination of Fluorescent Proteins

A test was carried out in the same manner as in the experiment (3), but a florescent protein combination different from that of the experiment (3), as shown in FIG. 19, was fused to IkBα, RelA and ferritin protein.

The recombinant genes FRB-mRFP-FT, FKBP-YFP-RelA and IkBα-ECFP-FKBP were introduced together into Hela cells, and then the ferritin fusion protein was expressed in the cells. As the cells were treated with Rapamycin, the FRB and FKBP proteins interacted with each other, while the IkBα and RelA proteins interacted with each other, thus forming a large nano-assembly matrix in the cells.

As a result, as shown in FIG. 19, the nano-assembly matrix formed by the interaction between the IkBα and RelA proteins was not influenced even when various combinations of fluorescent proteins were attached to each of the proteins.

Example 3

Formation of Nano-Assembly Matrix Through Interaction Between Proteins by Physiological Signal A test was carried out in order to examine whether the interaction between proteins, which are regulated according to an external signal, can be analyzed. As a material that mediates (regulates) the interaction between the prey and the bait, an external signal was used.

The recombinant genes FRB-ECFP-FT, FKBP-mRFP-bTrCP and IkBα-YFP-FKBP were introduced together into Hela cells, and each of the fusion proteins was expressed in the cells. Although IkBα used in Example 2 always interacts with the RelA protein regardless of the external stimulation of cells, it interacts with the bTrCP protein, only when a physiological external signal of TNFa was transferred to cells. For this reason, cells were treated with TNFa.

As a result, as shown in FIG. 20, the IkBα and bTrCP proteins interacted with each other, and the FRB and FKBP proteins as mediator (regulator) materials interacted with each other by treatment with another mediator (regulator) material Rapamycin, thus forming a nano-assembly matrix of ferritin in the cells.

In another example, IKKb-IkBα proteins were used as prey-bait, and TNFa was used as a material for mediating (regulating) the interaction between them. The IkBα and IKKb proteins interact with each other, only when a physiological external signal of TNFa is transferred to cells. The interaction between phosphorylase (such as IKKb) and IkBα that is the substrate thereof is known as one of the weakest interactions in cells. The recombinant genes FRB-ECFP-FT, IKKb-mRFP-FKBP and IkBα-YFP-FKBP were introduced together into Hela cells, and each of the fusion proteins was expressed in the cells. As a result, as shown in FIG. 21, a large nano-assembly matrix was formed in cells through the interaction between the IkBα and IKKb proteins by treatment with TNFa.

From the above results, it was found that the interaction between very sensitive detection molecules, which occurs in cells by a physiological signal, can be analyzed through a nano-assembly matrix.

Example 4

Formation of Nano-Assembly Matrix by Interaction Between RNA and Protein

As shown in FIG. 22, an experiment was designed such that a nano-assembly matrix is formed through the interaction between RNA and a regulator protein.

A protein Ago2 used in the experiment is a regulator protein interacting with miRNA and consists of several domains. Among such domains, a PAZ domain is important in interaction with miRNA. A ferritin fusion protein having this domain can interact with miRNA, and miRNA binds specifically to a target mRNA. The experiment was designed such that, when an MS2 binding sequence is attached to the terminal end of the target mRNA, it interacts with the ferritin fusion protein including the MS2 protein, that is, miRNA binds to the target mRNA, thus forming a large nano-assembly matrix.

First, based on the PAZ domain and PiWi domain of the regulator protein Ago2 which interacts with miRNA, a full-length mutant, a PAZ-PiWi domain-deletion mutant, a PiWi domain-deletion mutant and a PAZ domain-deletion mutant were constructed. Then, an MS2 binding sequence (5'-AAA CAT GAG GAT CAC CCA TGT-3': SEQ ID NO: 1) to which the MS2 protein can bind was attached to the terminal end of lin28-MS2bs which is the target mRNA, thus constructing MS2CP-mRFP-FT.

PAZ-CFP-FT, lin28-MS2bs(mRNA) and MS2CP-mRFP-FT were introduced into Hela cells by electroporation, and then expressed in the cells for 16 hours. Then, an expression vector of let7b miRNA was additionally introduced into the cells, and after 20 hours, the cells were observed.

As a result, as shown in FIG. 23, a large nano-assembly matrix was formed through the binding between the PAZ-CFP-FT fusion protein and miRNA, the binding between let-7b(miRNA) and lin28-MS2bs(mRNA) and the binding between lin28-MS2bs(mRNA) and MS2CP-mRFP-FT (ferritin fusion protein).

Example 5

High-Throughput Screening of Formation of Nano-Assembly Matrix

In order to detect and screen the interaction between various bioactive molecules, an HTS (High Throughput Screening) system was used (FIG. 24).

To establish the system, Hela cells were cultured in a 96-well plate (Greiner bio-one), and then FKBP-mRFP-FT and FRB-EGFP-FT genes were introduced simultaneously and expressed in the cells. After 24 hours, only 12 wells among 96 wells were selected and treated with 250 nM of Rapamycin for 30 minutes, and the formation of a nano-assembly matrix through the interaction between FRB and FKBP by Rapamycin was imaged at high speed using In-Cell Analyzer 1000 (GE).

The formation of a nano-assembly matrix through the interaction between FRB and FKBP by Rapamycin in the 96-well plate was examined using In-Cell Analyzer 1000 (GE) (FIG. 25). In the wells treated with 250 nM of Rapamycin for 30 minutes, the FKBP and FRB proteins fused to the ferritin protein in the cytoplasm interacted with each other to form a nano-assembly matrix, whereas, in the wells not treated with Rapamycin, a nano-assembly matrix of ferritin was not formed even after 30 minutes, and the proteins were uniformly spread in the cytoplasm.

The cells were fixed with 3.5% paraformaldehyde, the nuclei were stained with Hoechst, and the formation of a nano-assembly matrix obtained in the 96-well plate was systemically analyzed. Using an algorithm of In-Cell Developer (GE), the formation of a nano-assembly matrix through the interaction between FRB and FKBP by Rapamycin was recognized as a granule, and the imaging results were effectively and quantitatively analyzed and screened. The screening and quantification could be effectively performed using the percent (%) of cells having nano-assembly matrices formed therein, in each well of the 96-well plate, or the number of nano-assembly matrices per cell (FIG. 26).

Example 6

Examination of Interaction of Detection Molecules on Nano-Assembly Matrix Whose Formation was Induced Using Specific Mutations as Mediator (Regulator) Materials (1) Formation of Nano-Assembly Matrix by Interaction Between Mutated FKBP and FKB The FKBP proteins were mutated, such that the formation of nano-assembly matrices was spontaneously induced through the binding between the proteins.

The $36^{th}$ amino acid phenylalanine of FKBP was replaced with methionine, such that the monomeric FKBP was changed into a dimeric form. Such mutant FKBP was fused to ferritin, and FKBP(F36M)-mRFP-FT and FRB-EGFP fusion proteins were expressed in Hela cells in order to examine the spontaneous formation of nano-assembly matrices in the cells (FIG. 28). Also, the formed nano-assembly matrices were treated with 250 nM of Rapamycin.

As a result, it could be seen that the interaction between FKBP(F36M) and FRB on the surface of the nano-assembly matrix was induced, and FRB-EGFP were rapidly bound and docked or recruited to the surface of the nano-assembly matrix within 10 minutes (FIG. 28). Namely, the FKBP functioned as a mediator (regulator) by mutation and, at the same time, functioned as a bait which interacted with FRB (prey).

In addition, in order to examine whether the interaction between detection molecules (FKBP(F36M)-FRB) is specific to Rapamycin that is a material regulating the interaction, 25 μM of FK506 was used as a competitive compound for the interaction between FKBP(F36M) and Rapamycin.

As a result, as shown in FIG. 29, FRB-EGFP was detached from the surface of the nano-assembly matrix. This suggests that the process of docking of FKBP(F36M) and FRB can be reversibly regulated. In addition, it was confirmed that the interaction between the detection molecules FKBP-FRB specifically occurred through the mediator (regulator) material Rapamycin.

(2) Detection of DFX-DHFR Interaction

In the same manner as in the experiment (1), the recombinant genes FKBP(F36M)-mRFP-FT and DHFR-mRFT-FT were introduced together into Hela cells, and the ferritin fusion proteins were expressed in the cells. Then, the cells were treated with 10 μM of MTX-BODIPY@FL. Specifically, the formation of nano-assembly matrices was induced by the FKBP(F36M) mutant protein, and the DHFR protein (bait) was attached to the ferritin protein, such that it was exposed to the surface of the nano-assembly matrices, and then the DHFR protein was expressed in the cells. The distribution of the ferritin fusion proteins in the cells was analyzed with a fluorescence microscope (FIG. 30).

In the above state, the cells were treated with an MTX compound (prey) having a BODIPY dye attached thereto, and then whether MTX binds to DHFR was analyzed at varying points of time.

As a result, as shown in FIG. 30, it was observed that, in the case of nano-assembly matrices having no DHFR, MTX was not docked or recruited to the nano-assembly matrices, whereas, in the case of nano-assembly matrices having DHFR on the surface thereof, the MTX compound was bound and docked to the nano-assembly matrices from about 1 hour after treatment with the MTX compound.

FIG. 31 is a photograph showing that, at 150 minutes after treatment with the MTX compound, the MTX compound was bound and docked to the surface of the nano-assembly matrices having DHFR in the cells.

Test Example 6-1

Nano-Assembly Matrices Whose Formation is Induced Depending on Number of FKBP(F36M) Mutant Proteins Attached In order to optimize the induction of formation of nano-assembly matrices by an FKBP(F36M) mutant-ferritin fusion protein, the number of FKBP(F36M) mutant proteins attached was continuously increased to 6, while the results of expression thereof were observed.

As a result, as shown in FIG. 32, nano-assembly matrices were effectively formed from 12 hours after the expression of the protein in the cells, when the number of mutant proteins attached was more than 2. However, when the number of mutant proteins attached was more than 4, the intracellular expression of the mutant proteins was significantly reduced.

Test Example 6-2

Nano-Assembly Matrices Whose Formation is Induced Depending on Number of FKBP(F36M) Mutant Proteins and Time In the same manner as in Test Example 6-1, the number of the FKBP(F36M) mutant proteins was increased from 1 to 3, while the mutant protein was fused to ferritin to induce the spontaneous formation of nano-assembly matrices. The pattern of the formation was observed at varying points of time.

As a result, as shown in FIG. 33, when the number of the FKBP(F36M) mutant proteins is 1, nano-assembly matrices started to be formed 36 hours after introduction of the proteins into Hela cells, whereas, when the number of the mutant proteins is 2 or 3, nano-assembly matrices were effectively formed within 12 hours after introduction of the proteins into the cells.

From the above test results, conditions for optimizing the induction of formation of nano-assembly matrices by the FKBP(F36M) mutant-ferritin fusion protein could be anticipated.

Example 7

Examination of Detection Molecules on Nano-Assembly Matrices Whose Formation was Induced Using Interaction Between Specific Compound and Protein as Mediator (Regulator) Material In this experiment, a FKBP (wild type) protein was used as a material for inducing the formation of nano-assembly matrices, while an AP1510 compound was used as a material for mediating the binding between FKBP proteins. The AP1510 compound is a FK506-like compound and is a mediator (regulator) material, which has two moieties capable of binding to the FKBP protein, linked with each other by a linker, such that it can interact simultaneously with two molecules of the FKBP protein.

Two FKBP (wild type) proteins were continuously fused to ferritin and expressed in Hela cells. The cells were treated with 1 μM of the AP1510 compound, which is an FKBP interaction mediator (regulator) material, and the formation of nano-assembly matrices within 1 hour was observed through In-Cell Analyzer 1000 (GE) (FIG. 35). After the formation of the nano-assembly matrices was induced for 3 hours, the cells were treated with 250 nM of Rapamycin for 1 hour.

As a result, it was seen that the FRB protein (prey) interacted with FKBP, such that it was bound and docked or recruited to the surface of the nano-assembly matrices (FIGS. 35 and 37).

Herein, FKBP functioned as a mediator (regulator) material of forming nano-assembly matrices by interaction with the AP1510 compound and, at the same time, functioned as a bait interacting with FRB (prey).

Test Example 7-1

Nano-Assembly Matrices which are not Influenced by Kind of Fluorescent Protein Attached For the case where mRFP was attached to the FKBP protein in Example 7, various fluorescent proteins, such as ECFP, TagCFP and mTFP1, were attached to the FKBP protein to examine the effect of the AP1510 compound on the induction of formation of nano-assembly matrices.

FKBP was fused to the ferritin protein, and the three different fluorescent proteins were attached between FKBP and ferritin, and then expressed in Hela cells. After 24 hours of expression, each of the cells was treated with 1 μM of the AP1510 compound.

As a result, as shown in FIG. 36, the formation of nano-assembly matrices was induced more effectively in the case of TagCFP-mTFP1 and mTFP1 than the case of ECFP by the AP1510 compound. Moreover, as shown in FIG. 37, it was observed that, in the case of TagCFP, when the nano-assembly matrices whose formation has been induced by the AP1510 compound was treated with Rapamycin, the FRB protein (prey) (a partner detection material for FKBP) interacted with FKBP, such that it was docked or recruited to the surface of the nano-assembly matrices.

INDUSTRIAL APPLICABILITY

As described above, according to the present invention, the interaction between various bioactive molecules can be detected either by analyzing whether nano-assembly matrices are formed through the interaction between the bioactive molecules in the same field or system in vivo or by analyzing whether the bioactive molecules co-localize on the nano-assembly matrices. Accordingly, the present invention can be applied to kits or chips for detecting the interaction between a "bait" and a "prey" in vitro and in vivo.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for detecting molecular interactions within living cells, comprising the steps of:
   (i) providing into said living cells ferritin of same types or different types, having a bait bound thereto and other ferritin of same types or different types, having a prey bound thereto to the same field or system,
   wherein the ferritin is a protein having a plurality of the same or different binding moieties and can be assembled by the self-assembly between them; wherein the ferritin having a bait bound thereto and the ferritin having a prey bound thereto are the same or different types;
   (ii) forming a nano-assembly matrix by the interaction between the bait and the prey; and
   (iii) examining whether the nano-assembly matrix was formed, thus detecting the bait-prey interaction.

2. The method for detecting molecular interactions according to claim 1, wherein the interaction between the bait and the prey occurs directly or indirectly in step (i).

3. The method for detecting molecular interactions according to claim 1, wherein a material capable of mediating or regulating the interaction between the bait and the prey is additionally added in step (i).

4. The method for detecting molecular interactions according to claim 1, wherein each of the bait and the prey is provided in a state in which a label is bound thereto.

5. The method for detecting molecular interactions according to claim 3, wherein the material capable of mediating or regulating the interaction between the bait and the prey is provided in a state in which a label is bound thereto.

6. A method for detecting molecular interactions within living cells, comprising the steps of:
   (i) providing into said living cells ferritin of same types or different types, having a bait and mediator (regulator) materials bound thereto, to the same field or system,
   wherein the ferritin is a protein having a plurality of the same or different binding moieties and can be assembled by the self-assembly between them,
   wherein the ferritin form a nano-assembly matrix by the interaction between the mediator materials;
   (ii) providing a prey to the same field or system; and
   (iii) examining whether the prey co-localizes with the formed nano-assembly matrix by interacting with the bait present on the formed nano-assembly matrix, thus detecting the bait-prey interaction.

7. A method for detecting molecular interactions within living cells, comprising the steps of:
   (i) providing into said living cells ferritin of same types or different types, having first mediator (regulator) materials bound thereto, and a bait having second mediator (regulator) molecules bound thereto, to the same field or system,
   wherein the ferritin is a protein having a plurality of the same or different binding moieties and can be assembled by the self-assembly between them,
   wherein the ferritin form a nano-assembly matrix-first mediator (regulator) materials complex by the interactions between the first mediator (regulator) materials, and the bait having second mediator molecules is bound to the formed nano-assembly matrix-first mediator (regulator) materials complex by the interaction between the second mediator materials and the first mediator material of the formed nano-assembly matrix;
   (ii) providing a prey to the same field or system; and
   (iii) examining whether the prey co-localizes with the formed nano-assembly matrix by interacting with the bait bound to the formed nano-assembly matrix, thus detecting the bait-prey interaction.

8. The method for detecting molecular interactions according to claim 6 or 7, wherein a material mediating or regulating the interactions between the mediator (regulator) materials is additionally added in step (i).

9. The method for detecting molecular interactions according to claim 6 or 7, wherein a material which mediating or regulating the interaction between the bait and the prey is additionally added in step (iii).

10. The method for detecting molecular interactions according to claim 6 or 7, wherein each of the bait, the prey and the mediator (regulator) material is provided in a state in which a label is bound thereto.

11. The method for detecting molecular interactions according to any one claim among claims 1, 6 and 7, wherein the bait, the prey and/or the mediator (regulator) material is a bioactive molecule.

12. The method for detecting molecular interactions according to claim 11, wherein the bioactive molecule is selected from the group consisting of nucleic acids, nucleotides, proteins, peptides, amino acids, saccharides, lipids, vitamins and chemical compounds.

13. The method for detecting molecular interactions according to claim 4 or 5, wherein the label is a radioactive label, a fluorescent material or a luminescent material.

14. The method for detecting molecular interactions according to claim 13, wherein the fluorescent material is a fluorescent dye, a tetracystein motif, a fluorescent protein, or a fluorescent nanoparticle.

15. The method for detecting molecular interactions according to claim 10, wherein the label is a radioactive label, a fluorescent material or a luminescent material.

16. The method for detecting molecular interactions according to claim 15, wherein the fluorescent material is a fluorescent dye, a tetracystein motif, a fluorescent protein, or a fluorescent nanoparticle.

17. The method for detecting molecular interactions according to any one claim among claims 1, 6 and 7, wherein the living cells are selected from the group consisting of Zebra fish, *C. elegans*, yeast, fly or frog, mammal (except human) and plant.

18. The method for detecting molecular interactions according to any one claim among claims 1, 6 and 7, wherein the step of providing ferritin into the living cells is carried out by the use of any one selected from the group consisting of transducible peptide (or fusogenic peptide), lipid (or liposome) gene transporter or the binding complex thereof; electroporation and magnetofection.

19. The method for detecting molecular interactions according to any one claim among claims 1, 6 and 7, wherein the formation of nano-assembly matrix is examined using any one selected from the group consisting of an optical means, a scanner, a radioactive label detecting device, a fluorescence polarization reader (FP reader), a spectrophotometer, MRI (magnetic resonance imaging), SQUID, MR relaxometer, a fluorescence detector, a luminescence detector.

20. The method for detecting molecular interactions according to any one claim among claims 1, 6 and 7, wherein the binding location of the prey by interaction with the bait is measured using any one selected from the group consisting of an optical means, a scanner, a radioactive label detecting device, a fluorescence polarization reader (FP reader), a spectrophotometer, MRI (magnetic resonance imaging), SQUID, MR relaxometer, a fluorescence detector, a luminescence detector.

21. A method for detecting a prey as a target, interacting with a bait within living cells, the method comprising the steps of:
(i) providing ferritin having a bait bound thereto and a library of prey bound to other ferritin, to the same field or system,
wherein the ferritin is a protein having a plurality of the same or different binding moieties and can be assembled by the self-assembly between them;
(ii) forming nano-assembly matrices by the interactions between the bait and a prey;
(iii) measuring whether the nano-assembly matrices were formed, thus detecting the interaction between the bait and the prey; and
(iv) selecting, isolating and identifying said prey as a target, which interacts with the bait to form nano-assembly matrices.

22. A method for detecting a prey as a target interacting with a bait within living cells, the method comprising the steps of:
(i) providing ferritin having a bait and mediator (regulator) materials bound thereto, to the same field or system,
wherein the ferritin is a protein having a plurality of the same or different binding moieties and can be assembled by the self-assembly between them,
wherein the ferritin form nano-assembly matrices by the interaction between the mediator (regulator) materials;
(ii) providing a prey library to the same field or system;
(iii) examining whether a prey co-localizes with the formed nano-assembly matrices by interacting with the bait present on the formed nano-assembly matrices, thus detecting the bait-prey interaction;
and
(iv) selecting, isolating and identifying said prey as a target, which interacts with the bait to co-localize with the formed nano-assembly matrices.

23. A method for detecting a prey as a target interacting with a bait within living cells, the method comprising the steps of:
(i) providing ferritin having first mediator (regulator) materials bound thereto, and a bait having second mediator (regulator) materials bound thereto, to the same field or system,
wherein the ferritin is a protein having a plurality of the same or different binding moieties and can be assembled by the self-assembly between them,
wherein the ferritin form nano-assembly matrices by the interaction between the first mediator (regulator) materials and the bait having second mediator molecules is bound to the formed nano-assembly matrices by the interaction between the second mediator (regulator) material and the first mediator material of the formed nano-assembly matrix;
(ii) providing a prey library to the same field or system;
(iii) examining whether a prey co-localizes with the formed nano-assembly matrix by interacting with the bait bound to the formed nano-assembly matrix, thus detecting the bait-prey interaction; and
(iv) selecting, isolating and identifying said prey as a target, which interacts with the bait to co-localize with the formed nano-assembly matrices.

24. The method for detecting a prey as a target interacting with a bait according to claim 21, wherein the interaction between the bait and the prey occurs directly or indirectly in step (i).

25. The method for detecting a prey as a target interacting with a bait according to claim 21, wherein a material capable of mediating or regulating the interaction between the bait and the prey is additionally added in step (i).

26. The method for detecting a prey as a target interacting with a bait according to claim 22 or 23, wherein a material mediating or regulating the interactions between the mediator (regulator) materials is additionally added in step (i).

27. The method for detecting a prey as a target interacting with a bait according to claim 22 or 23, wherein a material mediating or regulating the interaction between the bait and the prey is additionally added in step (iii).

28. The method for detecting a prey as a target interacting with a bait according to any one claim among claims 21-23, wherein each of the bait, the prey and the mediator (regulator) material is provided in a state in which a label is bound thereto.

29. A method for detecting a target molecule which blocks (inhibits) or activates (induces) the interaction between a bait and a prey within living cells, the method comprising the steps of:
(i) providing ferritin having a bait bound thereto and other ferritin having a prey bound thereto, to the same field or system, wherein the ferritin is a protein having a plurality of the same or different binding moieties and can be assembled by the self-assembly between them;

(ii) forming nano-assembly matrices by the interaction between said bait and said prey in the presence of target candidates; and (iii) selecting, as a target blocker molecule or a target activator molecule, a target candidate corresponding to a case in which the degree of co-localization of said bait with said prey in the presence of the target candidate is blocked (inhibited) or activated (induced) compared to the degree of co-localization of said bait with said prey in the absence of the target candidate.

30. A method for detecting a target molecule which blocks (inhibits) or activates (induces) the interaction between a bait and a prey within living cells, the method comprising the steps of:

(i) providing ferritin having a bait and mediator (regulator) materials bound thereto, to the same field or system, wherein the ferritin is a protein having a plurality of the same or different binding moieties and can be assembled by the self-assembly between them;

(ii) forming nano-assembly matrices by the interactions between said mediator (regulator) materials in the presence of target candidates;

(iii) providing a prey to the same field or system;

(iv) selecting, as a target blocker molecule or a target activator molecule, a target candidate corresponding to a case in which the degree of co-localization of the formed nano-assembly matrices with said prey in the presence of the target candidate is blocked (inhibited) or activated (induced) compared to the degree of co-localization of the formed nano-assembly matrices with said prey in the absence of the target candidate.

31. A method for detecting a target molecule which blocks (inhibits) or activates (induces) the interaction between a bait and a prey within living cells, the method comprising the steps of:

(i) providing ferritin having first mediator (regulator) materials bound thereto, and a bait having second mediator (regulator) materials bound thereto, to the same field or system, wherein the ferritin is a protein having a plurality of the same or different binding moieties and can be assembled by the self-assembly between them;

(ii) forming nano-assembly matrices by the interaction between said first mediator (regulator) materials in the presence of target candidates, and binding said bait having second mediator molecules to the formed nano-assembly matrices by the interaction between said second mediator (regulator) material and said first mediator material of the formed nano-assembly matrix;

(iii) providing a prey to the same field or system; and (iv) selecting, as a target blocker molecule or a target activator molecule, a target candidate corresponding to a case in which the degree of co-localization of the formed nano-assembly matrices with said prey in the presence of the target candidate is blocked (inhibited) or activated (induced) compared to the degree of co-localization of the formed nano-assembly matrices with said prey in the absence of the target candidate.

32. The method for detecting a target molecule which blocks (inhibits) or activates (induces) the interaction between a bait and a prey according to claim 29, wherein the interaction between the bait and the prey occurs directly or indirectly in step (i).

33. The method for detecting a target molecule which blocks (inhibits) or activates (induces) the interaction between a bait and a prey according to claim 29, wherein a material mediating or regulating the interaction between the bait and the prey is additionally added in step (ii).

34. The method for detecting a target molecule which blocks (inhibits) or activates (induces) the interaction between a bait and a prey according to claim 30 or 31, wherein a material mediating or regulating the interactions between the first mediator (regulator) materials, the interactions between the second mediator (regulator) materials, or the interactions between the first mediator (regulator) material and the second mediator (regulator) material, is additionally added in step (i).

35. The method for detecting a target molecule which blocks (inhibits) or activates (induces) the interaction between a bait and a prey according to claim 30 or 31, wherein a material mediating or regulating the interaction between the bait and the prey is additionally added in step (iii).

36. The method for detecting a target molecule which blocks (inhibits) or activates (induces) the interaction between a bait and a prey according to any one claim among claims 29-31, wherein each of the bait, the prey and the mediator (regulator) material is provided in a state in which a label is bound thereto.

* * * * *

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial
<220> FEATURE:
<223> OTHER INFORMATION: MS2 binding sequence

<400> SEQUENCE: 1
aaacatgagg atcacccatg t                                              21
```